United States Patent
Oki et al.

(10) Patent No.: US 7,828,947 B2
(45) Date of Patent: Nov. 9, 2010

(54) ARTIFICIAL LIPID MEMBRANE FORMING METHOD AND ARTIFICIAL LIPID MEMBRANE FORMING APPARATUS

(75) Inventors: Akio Oki, Kyoto (JP); Hiroaki Oka, Osaka (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 12/772,558

(22) Filed: May 3, 2010

(65) Prior Publication Data

US 2010/0213070 A1 Aug. 26, 2010

Related U.S. Application Data

(63) Continuation of application No. PCT/JP2009/003971, filed on Aug. 20, 2009.

(30) Foreign Application Priority Data

Aug. 26, 2008 (JP) .............................. 2008-216127

(51) Int. Cl.
- *G01N 27/327* (2006.01)
- *G01N 33/92* (2006.01)
- *B01L 3/00* (2006.01)

(52) U.S. Cl. ...................... 204/403.01; 204/403.08; 436/71; 422/99

(58) Field of Classification Search ............ 204/403.01, 204/403.08; 205/777.5, 778; 422/99, 100; 436/71

See application file for complete search history.

(56) References Cited

U.S. PATENT DOCUMENTS

2005/0214163 A1 9/2005 Kinpara et al.

(Continued)

FOREIGN PATENT DOCUMENTS

JP 07-241512 9/1995

(Continued)

OTHER PUBLICATIONS

Yasunobu Okada, "Patch Clamp Experimental Technique", Sep. 25, 1996, pp. 133-139, Yoshioka Book Store.

*Primary Examiner*—Alex Noguerola
(74) *Attorney, Agent, or Firm*—McDermott Will & Emery LLP

(57) ABSTRACT

An object of the present invention is to provide a method for easily forming an artificial lipid membrane in a short period of time and an artificial lipid membrane forming apparatus suitable for carrying out such method.

The present invention relates to a method for forming an artificial lipid membrane using an artificial lipid membrane forming apparatus. The apparatus comprises a substrate, a first spacer, a first thin film, a second spacer, a second thin film, and a cover, wherein a first chamber is formed between the substrate and the first thin film, the first thin film has a first through hole, a second chamber is formed between the first thin film and the second thin film, the second thin film has a second through hole, and the cover has an inlet. The method includes in this order a first electrolytic solution pouring step of pouring an electrolytic solution to the first chamber, a lipid solution pouring step of pouring a lipid solution to the first through hole or the second through hole, and a second electrolytic solution pouring step of pouring the electrolytic solution to the inlet to form the artificial lipid membrane inside the through hole to which the lipid solution is poured.

20 Claims, 16 Drawing Sheets

U.S. PATENT DOCUMENTS

2006/0251709 A1    11/2006    Ide
2007/0161101 A1    7/2007    Takeuchi
2008/0290323 A1    11/2008    Ide

FOREIGN PATENT DOCUMENTS

| | | |
|---|---|---|
| JP | 2005-91305 | 4/2005 |
| JP | 2005-098718 | 4/2005 |
| JP | 2005-185972 | 7/2005 |
| JP | 2005-245331 | 9/2005 |
| JP | 2005-315832 | 11/2005 |
| JP | 2006-312141 | 11/2006 |
| JP | 2007-029911 | 2/2007 |
| WO | WO 2005/071405 A1 | 8/2005 |
| WO | WO 2006/030523 A1 | 3/2006 |

(a)

(b)

(c)

(a)

(b)

(c)

(a)

(b)

(c)

(d)

(a)

(b)

(a)

(b)

(a)

(b)

(a)

(b)

(c)

ARTIFICIAL LIPID MEMBRANE FORMING METHOD AND ARTIFICIAL LIPID MEMBRANE FORMING APPARATUS

RELATED APPLICATIONS

This application is a Continuation Application of the U.S. National Phase under 35 U.S.C. §371 of International Application No. PCT/JP2009/003971, filed on Aug. 20, 2009, which in turn claims the benefit of Japanese Application No. 2008-216127, filed on Aug. 26, 2008, the disclosures of which Applications are incorporated by reference herein.

TECHNICAL FIELD

The present invention relates to a method for forming an artificial lipid membrane used in an analysis of membrane proteins, such as ion channels. The present invention also relates to an artificial lipid membrane forming apparatus suitable for carrying out such method.

BACKGROUND ART

Substance transportation between inside and outside of a cell is carried out through transmembrane proteins. It is known that among the transmembrane proteins, the ion channel causes a change in a membrane potential by permeation of ions, so that the ion channel plays an important role in information transmission by the generation of signals, such as a nerve action potential. Therefore, in recent years, there has been an increase in research into the ion channel.

An experimental method called a patch-clamp method is essential for the ion channel research, and the patch-clamp method was developed by Neher and Sakmann in 1976. In the patch-clamp method, first, a tip end of a minute glass tube called a patch electrode is caused to be in close contact with the surface of a cell membrane. A minute membrane region of an opening of the tip end of the minute glass tube is voltage-clamped with the minute membrane region electrically insulated from the other regions, and an ion current flowing through the ion channels contained in the minute membrane region is measured. The development of this method was useful for the identification of a functional element of a channel protein molecule and the elucidation of an operation mechanism and structure of the functional element. Thus, the patch-clamp method has brought significant innovations in physiological research.

Although the patch-clamp method is a highly effective method in the physiological research as described above, there are some cases to which the patch-clamp method cannot be applied. An examples of such case is a case where an access is anatomically difficult, i.e., a case of analyzing the channel on a minute structure, such as a channel on a cell organelle or a presynaptic membrane. In addition, the patch-clamp method is not applicable to a case where an experiment needs to be carried out with a simple configuration in order to advance research into the basic structure of the channel and the relationship between the detailed structure and function of the channel. In this case, the channel molecule needs to be analyzed by a simple system, i.e., a system composed of water, salt, phosphatide, and the channel.

As an effective method used when the patch-clamp method cannot be used, a lipid planar membrane method was developed. The lipid planar membrane method can be broadly classified into a foam spraying method and an attaching method (see NPL 1 for example).

FIG. 18 shows a conventional method for forming the artificial lipid membrane by the foam spraying method. In FIG. 18, a container 10 is divided by a flat plate 11 made from resin, such as Teflon (trademark) or polystyrene, having a hydrophobic surface, a space divided by the flat plate 11 is filled with an electrolytic solution 12, and a lipid solution 14, i.e., a liquid mixture of lipid molecules and an organic solvent is applied by a pipette 15 to a minute hole 13 opening on the flat plate 11. The excess organic solvent contained in the lipid solution 14 applied to the minute hole 13 gradually moves to a peripheral edge of the minute hole 13 to be removed. Thus, the artificial lipid membrane is formed in about 30 minutes to 3 hours.

When forming the artificial lipid membrane, saturated hydrocarbon, such as decane, hexadecane, or hexane, is typically used as the organic solvent. Phosphatide is typically used as the lipid. For example, diphytanoylphosphatidylcholine, or glycerol monooleate, is used.

FIGS. 19(a), 19(b), and 19(c) show another conventional method for forming the artificial lipid membrane by the attaching method. In FIG. 19(a), a container 20 is divided by a flat plate 21 made from resin, such as Teflon (trademark) or polystyrene, having a hydrophobic surface. As a pretreatment, squalene is applied to a minute hole 22 opening on the flat plate 21. An electrolytic solution 23 is added through an inlet 24 to one chamber of the container 20 such that the height of a liquid level of the electrolytic solution 23 does not exceed the height of a lower end of the minute hole 22. Next, a lipid solution, i.e., a liquid mixture of lipid molecules 25 and an organic solvent is dropped from above the container 20 to the electrolytic solution 23, and the solution is left for several minutes. As shown in FIG. 19(a), a lipid monomolecular membrane is formed at a gas-liquid interface of the electrolytic solution 23. The lipid molecule 25 has a hydrophilic portion and a hydrophobic portion, and the hydrophilic portion of the lipid molecule 25 is oriented toward the electrolytic solution 23.

Then, as shown in FIG. 19(b), the electrolytic solution 23 is added through the inlet 24 until the height of the liquid level of the electrolytic solution 23 exceeds the height of an upper end of the minute hole 22.

Next, the same operations as above are carried out in another chamber of the container 20. That is, an electrolytic solution 26 is added through an inlet 27 such that the height of the liquid level of the electrolytic solution 26 does not exceed the height of the lower end of the minute hole 22. Next, the lipid solution is added from above the container 20 to the electrolytic solution 26, and the solution is left for several minutes. The lipid monomolecular membrane is formed at the gas-liquid interface of the electrolytic solution 26. Then, the electrolytic solution 26 is added through the inlet 27 until the height of the liquid level of the electrolytic solution 26 exceeds the height of the upper end of the minute hole 22. By the above operations, the lipid monomolecular membrane formed later is attached to the lipid monomolecular membrane formed in advance at the minute hole 22. As a result, the artificial lipid membrane is formed at the minute hole 22.

However, forming the artificial lipid membrane stably and reproducibly by each of the above-described two methods requires a high degree of skill. As an easier method for forming the artificial lipid membrane, a method for utilizing a MEMS (Micro Electro Mechanical Systems) technology, or a semiconductor microfabrication technology to form the artificial lipid membrane on a small chip was devised (see PTL 1 for example).

FIG. 20 shows a conventional artificial lipid membrane forming apparatus described in PTL 1. In FIG. 20, a first chamber 31 and a second chamber 33 isolated from the first chamber 31 by a dividing wall 32 are provided. The dividing wall 32 has at least one small hole 34 which allows fluidic communication between the first chamber 31 and the second chamber 33. The artificial lipid membrane is formed in the following manner using the artificial lipid membrane forming apparatus shown in FIG. 20. First, the first chamber 31 is filled with a first aqueous solution, and the second chamber 33 is then filled with the lipid solution. The first aqueous solution and the lipid solution are caused to contact each other through the small hole 34. Further, the lipid solution in the second chamber 33 is replaced with a second aqueous solution. With this, an artificial lipid membrane 35 can be formed at the small hole 34.

Another artificial lipid membrane forming apparatus is disclosed in PTL 2. This artificial lipid membrane forming apparatus includes a third introducing port through which the lipid solution is introduced to a micro passage and a first introducing port and a second introducing port through which a first electrolytic solution and a second electrolytic solution, each containing a substance, such as a biologically-relevant substance, are introduced to a micro channel. Then, a molecular membrane is formed at an interface between the first electrolytic solution and the second electrolytic solution.

Further, still another artificial lipid membrane forming apparatus is disclosed in PTL 3. This artificial lipid membrane forming apparatus forms an artificial lipid membrane by covering a minute hole formed on a substrate. In this case, the artificial lipid membrane forming apparatus utilizes a closure phenomenon of the minute hole by a solvent to form the artificial lipid membrane. That is, the membrane is formed in such a state that the lipid solution is supplied onto the substrate on which the minute hole is formed, the substrate swells by the solvent, and the minute hole is closed. After that, the minute hole is opened by the evaporation of the solvent, and the artificial lipid membrane formed is extended. This artificial lipid membrane forming apparatus carries out a minute flow operation and causes the liquid mixture and the electrolytic solution to move at the interface.

Citation List

Patent Literature

PTL 1: Japanese Patent Laid-Open Publication No. 2005-098718 (page 15, FIG. 5)

PTL 2: Japanese Patent Laid-Open Publication No. 2005-185972 (page 73, FIG. 1)

PTL 3: Japanese Patent Laid-Open Publication No. 2005-245331 (page 14, FIG. 2)

Non Patent Literature

NPL 1: "Patch Clamp Experimental Technique" written by Yasunobu Okada, published on Sep. 25, 1996 by Yoshioka Book Store (pages 133-139)

SUMMARY OF INVENTION

Technical Problem

The conventional artificial lipid membrane apparatus realized on a small chip is complex and requires long time. This is because the conventional artificial lipid membrane forming apparatus adopts (1) a method for excessively supplying the lipid solution once and discharging it or (2) a method for supplying the lipid solution and the electrolytic solution through the same passage. Therefore, the method for discharging a surplus lipid solution is limited to (1) provide an external pump, a valve, or a flow control device or (2) stand by until an organic solvent in the lipid solution vaporizes or develops.

In PTL 1 for example, in order to sequentially supply the electrolytic solution and the liquid mixture of the lipid molecules and the organic solvent to the micro channel, a liquid supplying unit, such as a syringe pump, a diaphragm pump, or a peristaltic pump, provided outside the micro channel is used As with the artificial lipid membrane forming apparatus of PTL 1, the apparatus disclosed in PTL 2 uses a pressure applying unit and a flow rate adjusting unit to supply the electrolytic solution and the lipid solution.

Further, the apparatus disclosed in PTL 3 can supply the lipid solution and the electrolytic solution by interface movement, which is simple. However, discharging the lipid solution requires long time since it is necessary to stand by until the solvent evaporates.

An object of the present invention is to solve the above conventional problems and to provide a method and an apparatus, each of which is capable of easily forming an artificial lipid membrane in a short period of time.

Solution to Problem

To solve the above conventional problems, the present invention is a method for forming an artificial lipid membrane using an artificial lipid membrane forming apparatus comprising in the following order, an apparatus preparing step of preparing the apparatus comprising:
    a substrate;
    a first spacer disposed at one end of the substrate;
    a first thin film disposed on the substrate via the first spacer;
    a second spacer disposed at one end of the first thin film;
    a second thin film disposed on the first thin film via the second spacer; and
    a cover disposed at one end of the second thin film,
    wherein:
    a first chamber is formed between the substrate and the first thin film;
    the first thin film comprises a first through hole penetrating both surfaces thereof;
    a second chamber is formed between the first thin film and the second thin film;
    the second thin film comprises a second through hole penetrating both surfaces thereof;
    the cover has an inlet connected to the second through hole;
    the first through hole overlaps the second through hole in plan view; and
    the first chamber is connected to the inlet via the first through hole and the second through hole,
the method comprising in this order:
    a first electrolytic solution pouring step of pouring an electrolytic solution to the first chamber;
    a lipid solution pouring step of pouring a lipid solution through the second chamber to at least one of the first through hole or the second through hole; and
    a second electrolytic solution pouring step of pouring the electrolytic solution to the inlet to form the artificial lipid membrane inside the through hole to which the lipid solution is poured.

Moreover, the present invention is an artificial lipid membrane forming apparatus including: a substrate; a first spacer disposed at one end of the substrate; a first thin film disposed on the substrate via the first spacer; a second spacer disposed at one end of the first thin film; a second thin film disposed on the first thin film via the second spacer; and a cover disposed at one end of the second thin film, wherein: a first chamber is formed between the substrate and the first thin film; the first thin film has a first through hole penetrating both surfaces thereof; a second chamber is formed between the first thin film and the second thin film; the second thin film has a second through hole penetrating both surfaces thereof; the cover has an inlet connected to the second through hole; the first through hole overlaps the second through hole in plan view; and the first chamber is connected to the inlet via the first through hole and the second through hole.

In the present invention, it is preferable that the first thin film, the first spacer, and the second thin film be integrally formed.

In the present invention, it is preferable that a cross-sectional area of the first through hole be the same as a cross-sectional area of the second through hole.

In the present invention, it is preferable that the inlet overlap the first chamber in plan view.

In the present invention, it is preferable that an outer peripheral surface of the first chamber be hydrophilic.

In the present invention, it is preferable that an outer peripheral surface of the second chamber be hydrophobic.

In the present invention, it is preferable that an outer peripheral surface of the inlet be hydrophilic.

In the present invention, it is preferable that at least one of the first chamber and the inlet comprises an electrode.

In the present invention, it is preferable that at least one of the first chamber and the inlet comprises a sensor.

In the present invention, it is preferable that in the first electrolytic solution pouring step, the electrolytic solution be poured to the first chamber by capillarity.

In the present invention, it is preferable that in the lipid solution pouring step, the lipid solution be poured to at least one of the first through hole and the second through hole by capillarity.

In the present invention, it is preferable that an analyzing device use the method according to claim 1.

The above object, other objects, features and advantages of the present invention will be made clear by the following detailed explanation of preferred embodiments with reference to the attached drawings.

Advantageous Effects of Invention

In accordance with the artificial lipid membrane forming method and artificial lipid membrane forming apparatus of the present invention, an appropriate amount of lipid solution can be introduced to the through hole. Therefore, it is unnecessary to provide an outlet port through which the surplus lipid solution is discharged, and it is unnecessary to provide an external pump. In addition, it is unnecessary to stand by for a long period of time until the artificial lipid membrane is formed. As a result, the artificial lipid membrane can be easily formed in a short period of time as compared to the conventional artificial lipid membrane forming apparatus.

DESCRIPTION OF EMBODIMENTS

Embodiment 1

Hereinafter, one embodiment of the present invention will be explained in reference to the drawings.

Figure 1:
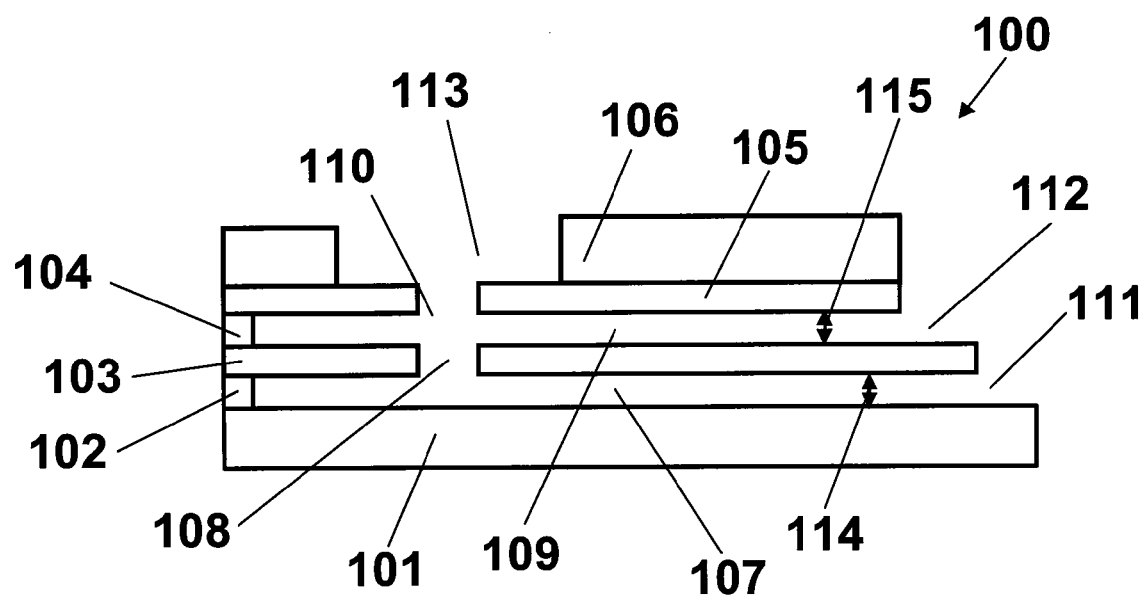
FIG. 1 shows a cross-sectional view of an artificial lipid membrane forming apparatus in Embodiment 1 of the present invention.
Figure 2:
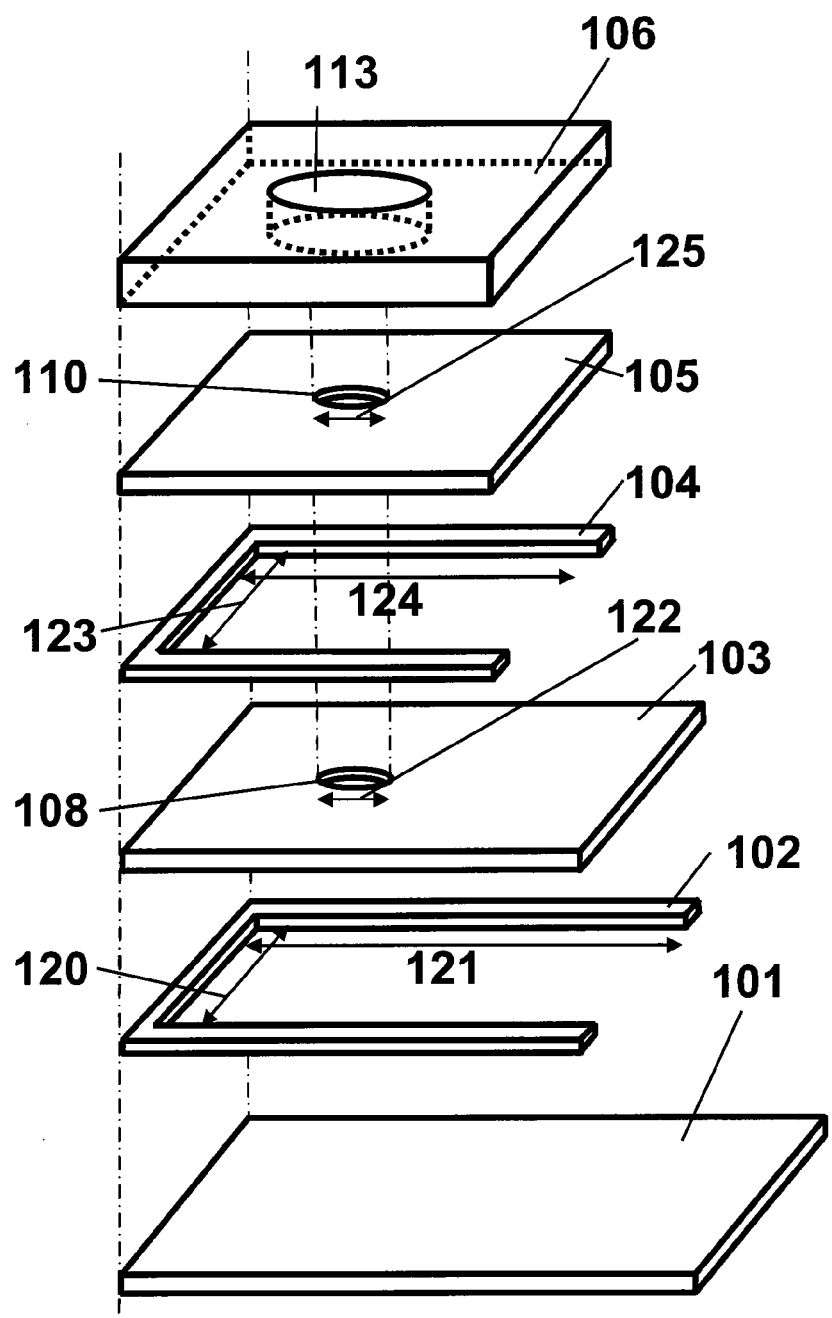
FIG. 2 shows an exploded oblique projection view of the artificial lipid membrane forming apparatus in Embodiment 1 of the present invention.
Figure 3:
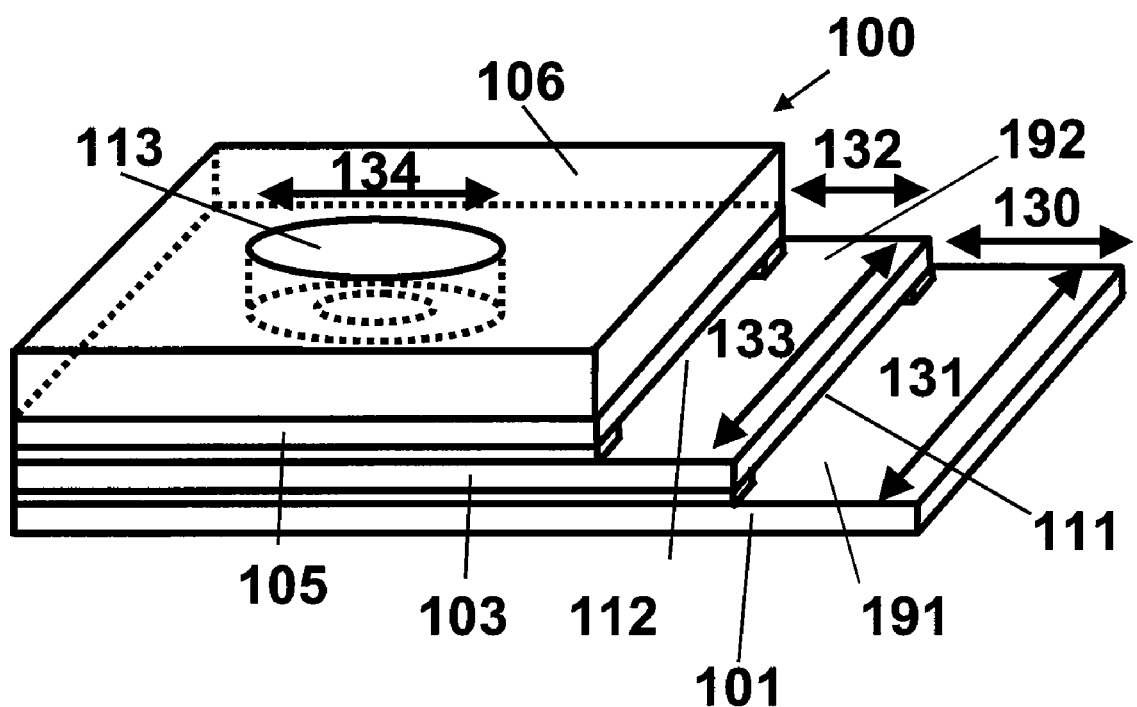
FIG. 3 shows an oblique projection view of the artificial lipid membrane forming apparatus in Embodiment 1 of the present invention.

FIGS. 1 to 3 show a cross-sectional view, an exploded oblique projection view, and an oblique projection view of an artificial lipid membrane forming apparatus in Embodiment 1 of the present invention, respectively.

In the present embodiment, an artificial lipid membrane forming apparatus 100 comprises a substrate 101. It is most preferable that a material of the substrate 101 be glass. The glass may be soda glass, quartz, borosilicate glass, low-melting-point glass, or photosensitive glass. The material of the substrate 101 may be the other inorganic material, such as silicon or aluminum oxide, an organic material, such as polyethylene, polypropylene, or vinyl chloride, or the other organic material. The material of the substrate 101 may be a combination of a plurality of materials. It is preferable that at least a part of an outer peripheral surface of the substrate 101 be a hydrophilic surface. In order to impart hydrophilicity to at least a part of the outer peripheral surface of the substrate 101, the part of the outer peripheral surface of the substrate 101 may be subjected to an oxygen plasma treatment or may be covered with a hydrophilic material. The part of the outer peripheral surface of the substrate 101 may be subjected to the other generally known hydrophilic treatment. It is preferable that the substrate 101 be transparent from the viewpoint of optical measurement. In the present invention, the shape of the substrate 101 is not limited.

A first spacer 102 is disposed on the substrate 101. A material of the first spacer 102 may be the organic material or the inorganic material. The most preferable organic material of the first spacer 102 is Teflon (trademark). The material of the first spacer 102 may be an organic polymer, such as polysulfone, polystyrene, polymethyl methacrylate, polyethylene, polyethylene terephthalate, vinyl chloride, or polydimethylsiloxane. Further, the material of the first spacer 102 may be plastic, such as polyethylene, polypropylene, or vinyl chloride. When using the organic material, an adhesive, such as a silicone adhesive, an epoxy adhesive, or a vinyl adhesive, a photoresist, a photosensitive organic material containing polyimide, or the like may be used.

When using the inorganic material, glass is preferable. The glass may be soda glass, quartz, borosilicate glass, or low-melting-point glass. When using the other inorganic material, silicon, silicon oxide, aluminum oxide, or silicon nitride may be used. The material of the first spacer 102 may be a combination of a plurality of materials.

It is preferable that at least a part of an outer peripheral surface of the first spacer 102 be a hydrophilic surface. It is preferable that the first spacer 102 be subjected to the hydrophilic treatment. In order to impart hydrophilicity to at least a part of the outer peripheral surface of the first spacer 102, the part of the outer peripheral surface of the first spacer 102 may be subjected to the oxygen plasma treatment or may be covered with the hydrophilic material. The part of the outer peripheral surface of the first spacer 102 may be subjected to the other generally known hydrophilic treatment. In the present invention, the shape of the first spacer 102 is not limited. However, generally, the first spacer 102 is disposed along an outer periphery of the substrate 101.

A first thin film 103 is disposed on the first spacer 102. Namely, the first spacer 102 is disposed between the substrate 101 and the first thin film 103. It is preferable that a material of the first thin film 103 be the organic material. The most preferable organic material of the first thin film 103 is Teflon (trademark). However, the material of the first thin film 103 may be the organic polymer, such as polysulfone, polystyrene, polymethyl methacrylate, polyethylene, polyethylene terephthalate, vinyl chloride, polydimethylsiloxane, or parylene. As the other organic material, an adhesive, such as a silicone adhesive, an epoxy adhesive, or a vinyl adhesive, a photoresist, or a photosensitive organic material containing polyimide may be used.

The first thin film 103 may be formed such that the inorganic material, such as glass, silicon oxide, or aluminum oxide is used as a base material, and the surface of the base material is covered with: the organic polymer, such as Teflon (trademark), polysulfone, polystyrene, polymethyl methacrylate, polyethylene, polyethylene terephthalate, vinyl chloride, polydimethylsiloxane, or parylene; an adhesive, such as a silicone adhesive, an epoxy adhesive, or a vinyl adhesive; a photoresist; a photosensitive organic material containing polyimide; or a self-assembled film (SAM) containing hydrocarbon. The material of the first thin film 103 may be a combination of a plurality of materials.

It is preferable that at least a part of an outer peripheral surface of the first thin film 103 be a hydrophobic surface. This is because the artificial lipid membrane becomes stable since a hydrophobic portion of a lipid molecule is held by the hydrophobic surface of the first thin film 103.

It is preferable that the first thin film 103 have a thickness of from 50 nm to 10 mm. It is more preferable that the first thin film 103 have a thickness of from 1 µm to 1 mm.

A second spacer 104 is disposed on the first thin film 103. That is, the first thin film 103 is disposed between the second spacer 104 and the first spacer 102. A material of the second spacer 104 may be the organic material or the inorganic material. The most preferable organic material of the second spacer 104 is Teflon (trademark). The material of the second spacer 104 may be the organic polymer, such as polysulfone, polystyrene, polymethyl methacrylate, polyethylene, polyethylene terephthalate, vinyl chloride, or polydimethylsiloxane. Further, the material of the second spacer 104 may be plastic, such as polyethylene, polypropylene, or vinyl chloride. When using the organic material, an adhesive, such as a silicone adhesive, an epoxy adhesive, a vinyl adhesive, a photoresist, or a photosensitive organic material containing polyimide may be used.

When using the inorganic material, glass is preferable. The glass may be soda glass, quartz, borosilicate glass, or low-melting-point glass. When using the other inorganic material, silicon, silicon oxide, aluminum oxide, or silicon nitride may be used. The material of the second spacer 104 may be a combination of a plurality of materials. It is preferable that at least a part of an outer peripheral surface of the second spacer 104 be a hydrophilic surface.

It is preferable that the second spacer 104 be subjected to the hydrophilic treatment. In order to impart hydrophilicity to at least a part of the outer peripheral surface of the second spacer 104, the part of the outer peripheral surface of the second spacer 104 may be subjected to the oxygen plasma treatment or may be covered with the hydrophilic material. The part of the outer peripheral surface of the second spacer 104 may be subjected to the other generally known hydrophilic treatment. In the present invention, the shape of the second spacer 104 is not limited. However, generally, the second spacer 104 is disposed along the outer periphery of the substrate 101.

A second thin film 105 is disposed on the second spacer 104. That is, the second spacer 104 is disposed between the second thin film 105 and the first thin film 103. It is preferable that a material of the second thin film 105 be an organic material. The preferable organic material of the second thin film 105 is plastic. The most preferable organic material is Teflon (trademark). The material of the second thin film 105 may be the organic polymer, such as polysulfone, polystyrene, polymethyl methacrylate, polyethylene, polyethylene terephthalate, vinyl chloride, polydimethylsiloxane, or parylene. As the other organic material, an adhesive, such as a silicon adhesive, an epoxy adhesive, or a vinyl adhesive, a photoresist, or a photosensitive organic material containing polyimide may be used.

The second thin film 105 may be formed such that the inorganic material, such as glass, silicon oxide, or aluminum oxide is used as a base material, and the surface of the base material is covered with: the organic polymer, such as Teflon (trademark), polysulfone, polystyrene, polymethyl methacrylate, polyethylene, polyethylene terephthalate, vinyl chloride, polydimethylsiloxane, or parylene; an adhesive, such as a silicone adhesive, an epoxy adhesive, or a vinyl adhesive; a photoresist; a photosensitive organic material containing polyimide; or a self-assembled film (SAM) containing hydrocarbon. The material of the second thin film 105 may be a combination of a plurality of materials.

It is preferable that at least a part of an outer peripheral surface of the second thin film 105 be a hydrophobic surface. This is because the artificial lipid membrane becomes stable since the hydrophobic portion of the lipid molecule is held by the hydrophobic surface of the second thin film 105.

It is preferable that the second thin film 105 have a thickness of from 50 nm to 10 mm. It is more preferable that the second thin film 105 have a thickness of from 1 µm to 1 mm.

A cover 106 is disposed on the second thin film 105. That is, the second thin film 105 is disposed between the cover 106 and the second spacer 104. It is preferable that a material of the cover 106 be an organic material. The preferable organic material of the cover 106 is polydimethylsiloxane. The organic material may be the organic polymer, such as polysulfone, polystyrene, polymethyl methacrylate, polyethylene, polyethylene terephthalate, vinyl chloride, polydimethylsiloxane, or parylene. Further, a photoresist or a photosensitive organic material containing polyimide may be used.

The material of the cover 106 may be the inorganic material, such as glass, silicon oxide, or aluminum oxide. It is preferable that at least a part of an outer peripheral surface of the cover 106 be a hydrophilic surface. However, the part of the outer peripheral surface of the cover 106 may be a hydrophobic surface. The material of the cover 106 may be a combination of a plurality of materials. It is preferable that the cover 106 be transparent from the viewpoint of the optical measurement. In the present invention, the shape of the cover 106 is not limited.

A first chamber 107 is formed between the substrate 101 and the first thin film 103. It is preferable that a height 114 of the first chamber 107 be from 10 nm to 100 mm, and it is more preferable that the height 114 be from 10 nm to 1 mm. In FIG. 2, it is preferable that a width 120 of the first chamber 107 be from 10 nm to 100 mm, and it is more preferable that the width 120 be from 1 µm to 5 mm. It is preferable that a length 121 of the first chamber 107 be from 10 nm to 100 mm, and it is more preferable that the length 121 be from 1 µm to 5 mm.

The height 114 of the first chamber 107 may be constant or may not be constant in the first chamber 107. Each of the width 120 and the length 121 of the first chamber 107 may be constant or may not be constant in the first chamber 107. In the present invention, the shape of the first chamber 107 is not limited. The most preferable shape of the first chamber 107 is a rectangular solid. However, the shape of the first chamber 107 may be the other shape, such as a column or a triangular prism.

A first through hole 108 is formed to penetrate both surfaces of the first thin film 103. The most preferable shape of the first through hole 108 when viewed from a normal direction of the first thin film 103 is a circle. However, the shape of the first through hole 108 may be the other shape, such as an ellipse, a square, a rectangle, a diamond shape, a hexagon, or a polygon.

It is preferable that a diameter 122 of the first through hole 108 be from 10 nm to 1 mm, and it is more preferable that the diameter 122 be from 2 µm to 200 µm.

A method for forming the first through hole 108 may be a machine work, such as cutting or punching, or may be lithography, etching, sand blasting, laser beam lithography, or nanoimprint.

It is preferable that an inner wall of the first through hole 108 be flat. However, a groove structure, or a concave-convex structure may be provided.

It is most preferable that the number of first through holes 108 be one. However, the number of first through holes 108 may be two or more. When two or more first through holes 108 are provided, the shapes of the first through holes 108 may be the same as or different from one another. When two or more first through holes 108 are provided, the diameters 122 of the first through holes 108 may be the same as or different from one another.

A second chamber 109 is formed between the first thin film 103 and the second thin film 105. The second chamber 109 is connected to the first chamber 107 via the first through hole 108. It is preferable that a height 115 of the second chamber 109 be from 10 nm to 1 mm, and it is more preferable that the height 115 be from 10 nm to 10 µm. In FIG. 2, it is preferable that a width 123 of the second chamber 109 be from 10 nm to 100 mm, and it is more preferable that the width 123 be from 1 µm to 5 mm. It is preferable that a length 124 of the second chamber 109 be from 10 nm to 100 mm, and it is more preferable that the length 124 be from 1 µm to 5 mm.

The height 115 of the second chamber 109 may be constant or may not be constant in the second chamber 109. For example, it is preferable that the height 115 of the second chamber 109 decrease in a direction away from an opening, since the lipid solution is poured in one direction. It is preferable that the height decreases in the vicinity of an outer peripheral edge of each of the first through hole 108 and a second through hole 110, since pouring of a surplus lipid solution can be suppressed.

Each of the width 123 and the length 124 of the second chamber 109 may be constant or may not be constant in the second chamber 109. In the present invention, the shape of the second chamber 109 is not limited. The most preferable shape of the second chamber 109 is a rectangular solid. However, the shape of the second chamber 109 may be the other shape, such as a column or a triangular prism. In order to control the pouring of the lipid solution, a groove structure or a concave-convex structure may be provided on an inner wall of the second chamber 109.

The second through hole 110 is formed to penetrate both surfaces of the second thin film 105. The most preferable shape of the second through hole 110 when viewed from a normal direction of the second thin film 105 is a circle. The shape of the second through hole 110 may be the other shape, such as an ellipse, a square, a rectangle, a diamond shape, a hexagon, or a polygon.

It is preferable that a diameter 125 of the second through hole 110 be from 10 nm to 1 mm, and it is more preferable that the diameter 125 be from 2 µm to 200 µm. It is preferable that the diameter 125 of the second through hole 110 be the same as the diameter 122 of the first through hole 108. However, the diameter 125 of the second through hole 110 may be different from the diameter 122 of the first through hole 108.

A method for forming the second through hole 110 may be a machine work, such as cutting or punching, or may be lithography, etching, sand blasting, laser beam lithography, or nanoimprint.

It is preferable that an inner wall of the second through hole 110 be flat. However, a groove structure, a concave-convex structure, or the like may be provided.

It is most preferable that the number of second through holes 110 be one. However, the number of second through holes 110 may be two or more. When two or more second through holes 110 are provided, the shapes of the second through holes 110 may be the same as or different from one another. When two or more second through holes 110 are provided, the diameters 125 of the second through holes 110 may be the same as or different from one another.

Figure 4:
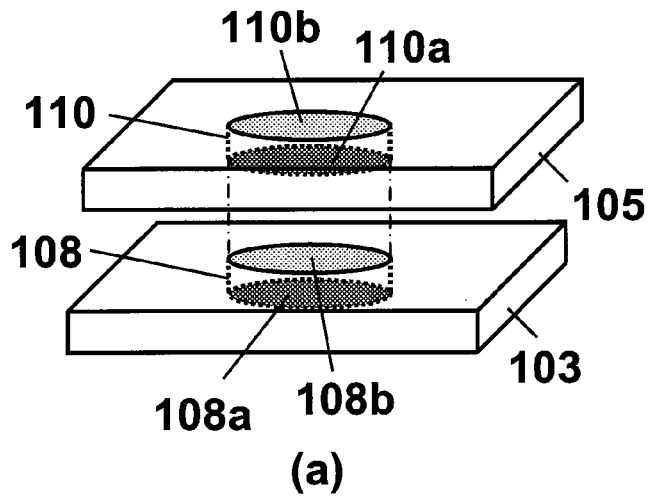
FIGS. 4 (*a*)-(*c*) show enlarged views of the artificial lipid membrane forming apparatus in Embodiment 1 of the present invention.
Figure 4:
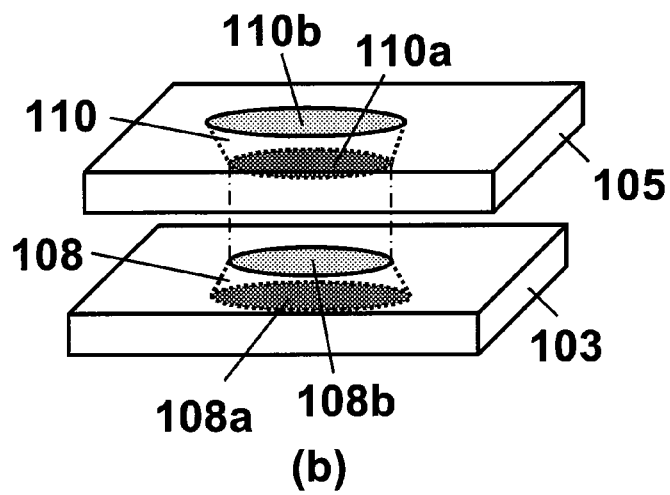
Figure 4:
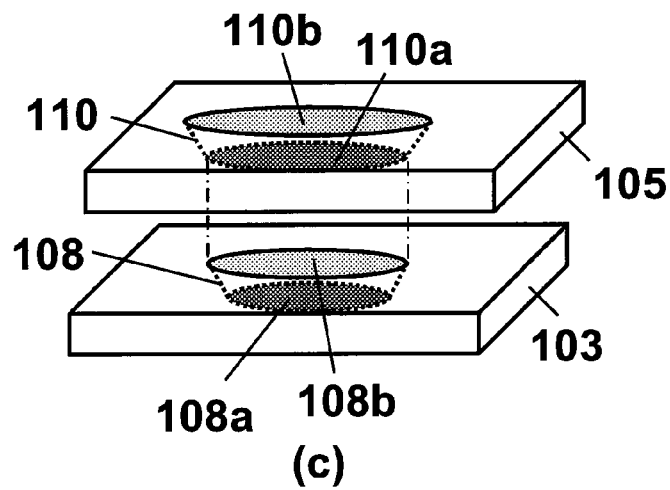

It is preferable that the first through hole 108 and the second through hole 110 be the same in shape as each other. The shape of each of the first through hole 108 and the second through hole 110 will be described below in detail. FIGS. 4(a) to 4(c) show enlarged views of the vicinity of each of the first through hole 108 and the second through hole 110 of the artificial lipid membrane forming apparatus in Embodiment 1 of the present invention. In FIGS. 4(a) to 4(c), for ease of explanation, only the first thin film 103 and the second thin film 105 are shown.

As shown in FIG. 4(a), it is most preferable that each of the first through hole 108 and the second through hole 110 has a column shape. It is preferable that the first through hole 108 and the second through hole 110 be the same in size as each other. It is preferable that the area of a cross section 108b of the first through hole 108 be substantially the same as the area of a cross section 110a of the second through hole 110. This is because the lipid solution is easily poured. It is preferable that a diameter of the cross section 108b of the first through hole 108 be from 10 nm to 1 mm, and it is more preferable that the diameter of the cross section 108b be from 2 µm to 200 µm. It is preferable that a diameter of the cross section 110a of the second through hole 110 be from 10 nm to 1 mm, and it is more preferable that the diameter of the cross section 110a be from 2 µm to 200 µm.

As shown in FIG. 4(b), at least one of the first through hole 108 and the second through hole 110 may have a trapezoidal column shape. The first through hole 108 and the second through hole 110 may be the same in size as each other. It is preferable that the area of the cross section 108b of the first through hole 108 be substantially the same as the area of the cross section 110a of the second through hole 110. It is preferable that the area of the cross section 108b of the first through hole 108 be smaller than the area of a cross section 108a of the first through hole 108. It is preferable that the area of the cross section 110a of the second through hole 110 be smaller than the area of a cross section 110b of the second through hole 110.

As shown in FIG. 4(c), each of the first through hole 108 and the second through hole 110 may have a trapezoidal column shape. It is preferable that the area of the cross section 108b of the first through hole 108 be substantially the same as the area of the cross section 110a of the second through hole 110. It is preferable that the area of the cross section 108b of the first through hole 108 be larger than the area of the cross section 108a of the first through hole 108. It is preferable that the area of the cross section 110a of the second through hole 110 be smaller than the area of the cross section 110b of the second through hole 110.

For simplicity, as shown in FIGS. 4(a) to 4(c), only the column shapes of the first through hole 108 and the second through hole 110 were explained. However, the same is true for the other shapes.

Figure 5:
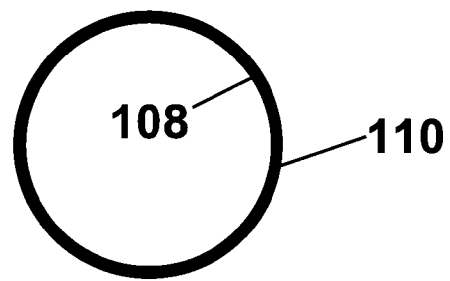
FIGS. 5 (*a*)-(*c*) show enlarged views of a first through hole and a second through hole in Embodiment 1 of the present invention.
Figure 5:
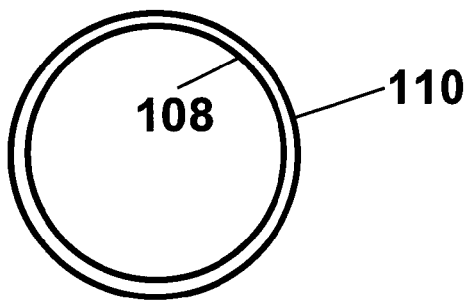
Figure 5:
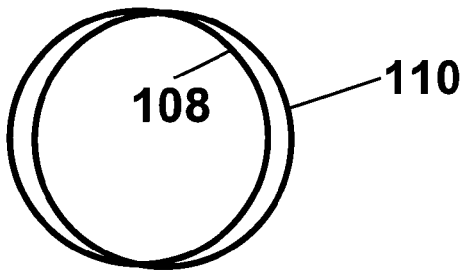

It is preferable that the first through hole 108 and the second through hole 110 be formed to overlap each other. A positional relation between the first through hole 108 and the second through hole 110 will be explained below in detail. FIGS. 5(a) to 5(c) are enlarged views of the first through hole 108 and the second through hole 110 in the artificial lipid membrane forming apparatus of Embodiment 1 of the present invention when viewed from a normal direction of the first thin film 103 and the second thin film 105. In FIGS. 5(a) to 5(c), for ease of explanation, only the first through hole 108 and the second through hole 110 are shown.

As shown in FIG. 5(a), it is most preferable that the first through hole 108 and the second through hole 110 coincide with each other. In the explanation of the present paragraph, for simplicity, the shape of each of the first through hole 108 and the second through hole 110 is the column.

As shown in FIG. 5(b), the first through hole 108 and the second through hole 110 may partially overlap each other. FIG. 5(b) shows that the diameter of the first through hole 108 is smaller than the diameter of the second through hole 110. However, the diameter of the first through hole 108 may be larger than the diameter of the second through hole 110.

As shown in FIG. 5(c), a center position of the first through hole 108 may not coincide with a center position of the second through hole 110. In this case, the diameter of the first through hole 108 may be different from the diameter of the second through hole 110.

When a plurality of first through holes 108 and a plurality of second through holes 110 are provided, they may be arranged in a linear fashion, a circumferential fashion, a radial fashion, in a square grid fashion, or in a triangle grid fashion.

As shown in FIG. 1, a first opening 111 is formed at one end of each of the substrate 101 and the first thin film 103. It is preferable that by causing the position of the end portion of the substrate 101 and the position of the end portion of the first thin film 103 to be different from each other, a first overhanging portion 191 be formed, and the first opening 111 be formed. It is preferable that a length 130 of the first overhanging portion 191 of the first opening 111 shown in FIG. 3 be from 1 to 10 mm. It is preferable that a width 131 of the first overhanging portion 191 of the first opening 111 be from 1 to 20 mm. The first opening 111 may be flat as shown in FIG. 3 or may include a groove structure or a concave-convex structure so as to facilitate the pouring of a liquid.

A second opening 112 is formed at one end of each of the first thin film 103 and the second thin film 105. As shown in FIG. 1, it is preferable that by causing the position of the end portion of the first thin film 103 and the position of the end portion of the second thin film 105 to be different from each other, a second overhanging portion 192 be formed, and the second opening 112 be formed. It is preferable that a length 132 of the second overhanging portion 192 of the second opening 112 shown in FIG. 3 be from 1 to 10 mm. It is preferable that a width 133 of the second overhanging portion 192 of the second opening 112 be from 1 to 20 mm. The second opening 112 may be flat as shown in FIG. 3 or may include a groove structure or a concave-convex structure so as to facilitate the pouring of a liquid.

An inlet 113 is formed at one end of the cover 106. The inlet 113 is connected to the second chamber 109 via the second through hole 110. As shown in FIG. 1, it is preferable that the inlet 113 be formed to penetrate the cover 106. As shown in FIG. 3, it is preferable that the shape of the inlet 113 be a column shape. However, the shape of the inlet 113 may be the other shape. It is preferable that when the shape of the inlet 113 is the column shape, a diameter 134 of the inlet 113 be from 0.5 to 2 mm.

The substrate 101 and the first spacer 102 may be integrally formed. The first spacer 102 and the first thin film 103 may be integrally formed. The first thin film 103 and the second spacer 104 may be integrally formed. The first spacer 102, the first thin film 103, and the second spacer 104 may be integrally formed. The first thin film 103, the second spacer 104, and the second thin film 105 may be integrally formed. The second spacer 104 and the second thin film 105 may be integrally formed. The second thin film 105 and the cover 106 may be integrally formed.

It is preferable that the substrate 101, the first spacer 102, the first thin film 103, the second spacer 104, the second thin film 105, and the cover 106 be joined to one another after they are laminated on one another. Respective layers may be bonded to one another using an adhesive or may be welded to one another by the application of heat. The laminated layers may be sandwiched between two plates to be fixed by bolts or may be joined to one another by the other method.

Figure 6:
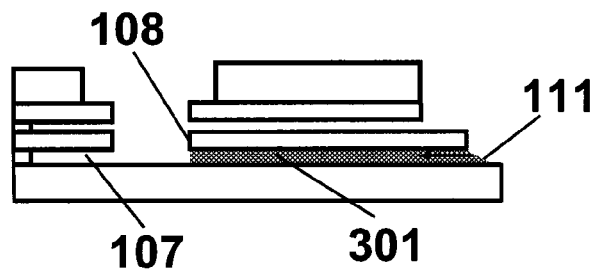
FIGS. 6 (*a*)-(*d*) show operation views of the artificial lipid membrane forming apparatus in Embodiment 1 of the present invention.
Figure 6:
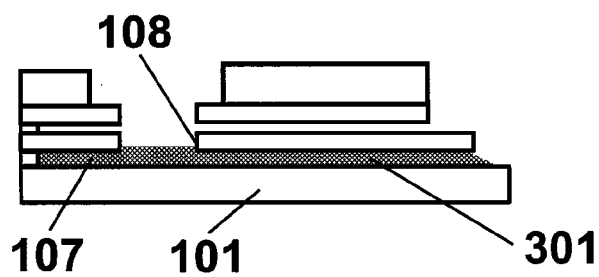
Figure 6:
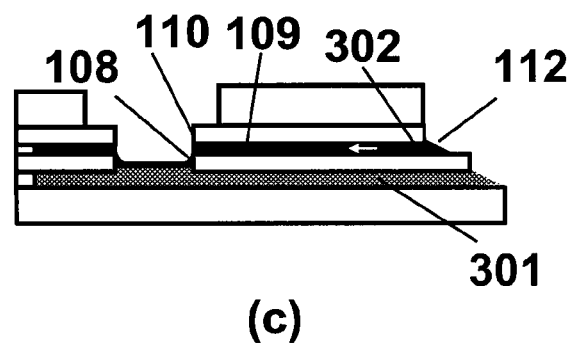
Figure 6:
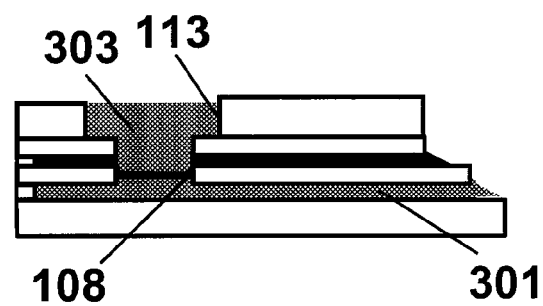

Next, a procedure of forming the artificial lipid membrane will be explained. FIG. 6 show operation views of the artificial lipid membrane forming apparatus in Embodiment 1 of the present invention. In FIG. 6, the same reference signs are used for the same components as in FIGS. 1 to 3, and explanations thereof are omitted.

First, FIGS. 6(a) and 6(b) show a first electrolytic solution pouring step. In the first electrolytic solution pouring step, a first electrolytic solution 301 is poured through the first opening 111 to the first chamber 107. It is preferable that the first electrolytic solution 301 contains KCl, and it is more preferable that the first electrolytic solution 301 is an isotonic KCl solution. It is preferable that the first electrolytic solution 301 has a physiological condition in a cell. It is preferable that pH be about 7. To adjust pH, a buffer solution, such as HEPES may be used. A solution typically used in an electrophysiological experiment may be used. It is preferable that a $Ca^{2+}$ concentration be from 10 to 100 nM. To adjust a $Ca^{2+}$ concentration, a $Ca^{2+}$ chelator, such as EGTA may be used. It is most preferable that the amount of first electrolytic solution 301 to be poured be about the same as the volume of the first chamber 107. However, the amount of first electrolytic solution 301 to be poured may be smaller or larger than the volume of the first chamber 107.

In the first electrolytic solution pouring step, it is most preferable that the first electrolytic solution 301 be poured to the first chamber 107 by capillarity. However, the first electrolytic solution 301 may be poured by its own weight or by the other method. FIGS. 6(a) and 6(b) show that the first electrolytic solution 301 is poured to the first chamber 107 by the capillarity. When the first electrolytic solution 301 is poured by the capillarity, as shown in FIG. 6(a), the first electrolytic solution 301 is sequentially poured from the first opening 111 toward the first through hole 108. Then, as shown in FIG. 6(b), the inside of the first chamber 107 is filled with the first electrolytic solution 301. It is preferable that when the first electrolytic solution 301 is poured to the first chamber 107 by the capillarity, at least a part of the outer peripheral surface of the substrate 101 be subjected to the hydrophilic treatment. It is preferable that a portion of the outer peripheral surface of the substrate 101 which portion contacts the first electrolytic solution 301 be subjected to the hydrophilic treatment. It is preferable that a portion of the outer peripheral surface of the substrate 101 which portion is located in the vicinity of the first through hole 108 be subjected to the hydrophilic treatment.

The first electrolytic solution pouring step may include a step of detecting the termination of the pouring of the first electrolytic solution 301 to the first chamber 107. In order to detect the termination of the pouring of the first electrolytic solution 301 to the first chamber 107, observation using an optical microscope may be carried out. The termination of the pouring of the first electrolytic solution 301 to the first chamber 107 may be detected such that a plurality of electrodes are provided in the first chamber 107 to measure an electric conductivity. The other typical method for detecting the existence of the electrolytic solution may be used.

Next, FIG. 6(c) shows a lipid solution pouring step. In the lipid solution pouring step, a lipid solution 302 is poured through the second opening 112 to the second chamber 109. It is most preferable that in the lipid solution pouring step, the lipid solution 302 be poured through the second chamber 109 to the first through hole 108. In the lipid solution pouring step, the lipid solution 302 may be poured through the second chamber 109 to the first through hole 108 and the second through hole 110. In the lipid solution pouring step, the lipid solution 302 may be poured through the second chamber 109 to the second through hole 110.

It is preferable that the lipid solution 302 be prepared by dispersing lipids in an organic solvent. It is most preferable that the lipids be phosphatide. The lipids may be glycolipids, lipo lipids, or the other lipids. The lipids may be azolectin, other naturally-derived lipids, or synthetic lipids. The synthetic lipids are more preferable since highly pure and chemically stable synthetic lipids are easily obtained. Specifically, the synthetic lipids may be phosphoric acid lipids, such as diphytanoyl phosphatidylcholine, glycerol monooleate, phosphatidylcholine, phosphatidyl ethanol amine, phosphatidylserine, or dipalmitoyl phosphatidylcholine, or may be the other phosphoric acid lipids. It is preferable that a fatty acid of the lipid molecule be a saturated fatty acid or an unsaturated fatty acid in each of which has 10 to 20 carbons. These lipids may be used alone or as a mixture of two or more. It is preferable that the concentration of the lipid in the organic solvent be from 3 to 50 mg/mL, and it is more preferable that it be from 4 to 40 mg/mL.

In addition to the lipids and the organic solvent, the lipid solution 302 may contain a material which gives a net surface electric charge to the artificial lipid membrane. It is preferable that the surface electric charge of the artificial lipid membrane be negative. In order to give the electric charge to the artificial lipid membrane, phosphatidylserine, or phosphatidyl inositol may be mixed. The material which gives the electric charge to the artificial lipid membrane may be mixed before the lipid solution pouring step or after an artificial lipid membrane forming step. In the present invention, the amount of material which gives the electric charge to the artificial lipid membrane is not limited.

In addition to the lipids and the organic solvent, the lipid solution 302 may contain a receptor, an ion channel, a biological membrane protein, such as G protein, or a secretory protein. Polypeptide, such as gramicidin, may be mixed in a lipid solution 302. Only one type or plural types of the biological membrane protein, the secretory protein, or the polypeptide may be mixed. The biological membrane protein, the secretory protein, or the polypeptide may be mixed before the lipid solution pouring step. The biological membrane protein, the secretory protein, or the polypeptide may be mixed after the artificial lipid membrane forming step.

When the biological membrane protein or the secretory protein is mixed after the artificial lipid membrane forming step, the biological membrane protein or the secretory protein may be once incorporated in a vesicle to cause the vesicle to fuse with the artificial lipid membrane, or a known mixing technology may be used. When mixing the biological membrane protein, the secretory protein, or the polypeptide after the artificial lipid membrane forming step, a mechanism configured to mix the biological membrane protein, the secretory protein, or the polypeptide may be provided in the artificial lipid membrane forming apparatus 100.

It is most preferable that in the lipid solution pouring step, the lipid solution 302 be poured to the second chamber 109 by the capillarity. In the lipid solution pouring step, the lipid solution 302 may be poured to the second chamber 109 by its own weight or by the other method.

It is preferable that in the lipid solution pouring step, the pouring of the lipid solution 302 to the second chamber 109 starts after the first chamber 107 is filled with the first electrolytic solution 301.

The lipid solution pouring step may include a step of detecting the termination of the pouring of the lipid solution 302 to the second chamber 109. In order to detect the termination of the pouring of the lipid solution 302 to the second chamber 109, observation using the optical microscope may be carried out. The other typical method for detecting the existence of the organic solvent or the lipid solution may be used.

Next, FIG. 6(d) shows a second electrolytic solution pouring step. In the second electrolytic solution pouring step, a second electrolytic solution 303 is poured to the inlet 113. It is preferable that the second electrolytic solution 303 contains KCl, and it is more preferable that the second electrolytic solution 303 is an isotonic KCl solution. It is preferable that the second electrolytic solution 303 has a physiological condition in a cell. It is preferable that pH be about 7. To adjust pH, a buffer solution, such as HEPES may be used. It is preferable that the $Ca^{2+}$ concentration be from 10 to 100 nM. To adjust the $Ca^{2+}$ concentration, $Ca^{2+}$ a chelator, such as EGTA may be used. It is most preferable that the amount of second electrolytic solution 303 to be poured be about the same as the volume of the inlet 113. However, the amount of second electrolytic solution 303 to be poured may be smaller or larger than the volume of the inlet 113. The second electrolytic solution 303 may be the same as or different from the first electrolytic solution 301.

Figure 7:
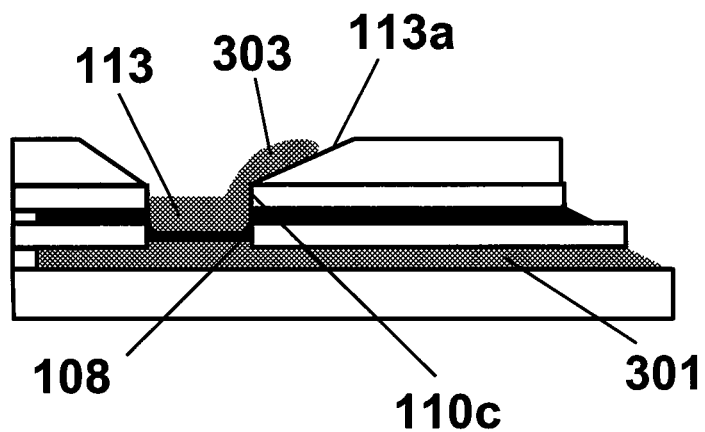
FIGS. 7 (*a*)-(*b*) show explanatory diagrams of a second electrolytic solution pouring step in Embodiment 1 of the present invention.
Figure 7:
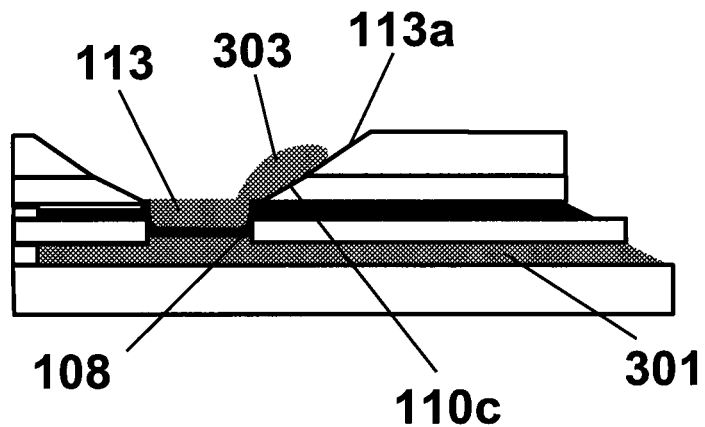

It is preferable that in the second electrolytic solution pouring step, an appropriate amount of the second electrolytic solution 303 be dropped to the inlet 113. FIGS. 7(a) and 7(b) show how the second electrolytic solution 303 is poured to the inlet 113 in the pouring step. As shown in FIG. 7(a), it is preferable that in order not to break the membrane of the lipid solution 302 formed at the first through hole 108 when dropping the second electrolytic solution 303 to the inlet 113, the second electrolytic solution 303 be poured along an inner wall surface 113a of the inlet 113. It is preferable that the inner wall surface 113a of the inlet 113 be inclined. It is preferable that an inner wall surface 110c of the second through hole 110 be inclined. As shown in FIG. 7(b), the inner wall surface 110c of the second through hole 110 may be inclined. An inclination angle of the inner wall surface 113a of the inlet 113 and an inclination angle of the inner wall surface 110c of the second through hole 110 may be the same as or different from each other. It is preferable that in order to facilitate the pouring of the second electrolytic solution 303, the inner wall surface 113a of the inlet 113 be subjected to the hydrophilic treatment. It is preferable that in order to facilitate the pouring of the second electrolytic solution 303, the inner wall surface 110c of the second through hole 110 be subjected to the hydrophilic treatment. The inner wall surface 113a of the inlet 113 may be flat or may include a groove structure or concave-convex structure so as to facilitate the pouring of the second electrolytic solution 303.

It is preferable that in the second electrolytic solution pouring step, the pouring of the second electrolytic solution 303 starts after the first through hole 108 is filled with the lipid solution 302. It is preferable that in the second electrolytic solution pouring step, the pouring of the second electrolytic solution 303 starts after the first through hole 108 and the second through hole 110 are filled with the lipid solution 302. It is preferable that in the second electrolytic solution pouring step, the pouring of the second electrolytic solution 303 start after the second through hole 110 is filled with the lipid solution 302.

The second electrolytic solution pouring step may comprise a step of detecting the termination of the pouring of the second electrolytic solution 303 to the inlet 113. In order to detect the termination of the pouring of the second electrolytic solution 303 to the inlet 113, observation using the optical microscope may be carried out. The termination of the pouring of the second electrolytic solution 303 may be detected such that a plurality of electrodes are provided in the inlet 113 to measure an electric conductivity. The other typical method for detecting the existence of the electrolytic solution may be used.

Thus, the artificial lipid membrane is formed at the first through hole 108. The artificial lipid membrane may be formed at the first through hole 108 and the second through hole 110. The artificial lipid membrane may be formed only at the second through hole 110. It is most preferable that the artificial lipid membrane be a lipid bilayer membrane. Herein, the organic solvent is removed from the thin film of the lipid solution 302 by the weight of the second electrolytic solution 303. It is preferable that the surplus organic solvent be removed along the outer peripheral surface of at least one of the first thin film 103 and the second thin film 105. In order to accelerate the removal of the organic solvent, a structure, such as a groove structure or a concave-convex structure, configured to control a minute fluid may be provided on the outer peripheral surface of at least one of the first thin film 103 and the second thin film 105, and in the vicinity of the first through hole 108 and the second through hole 110. In order to prevent the organic solvent from being removed more than necessary, a structure, such as a groove structure or a concave-convex structure, configured to control a minute fluid may be provided on the outer peripheral surface of at least one of the first thin film 103 and the second thin film 105 and in the vicinity of the first through hole 108 and the second through hole 110.

The artificial lipid membrane forming step may include a step of detecting the formation of the artificial lipid membrane. In order to detect the formation of the artificial lipid membrane, observation using the optical microscope may be carried out. The absorbance of the artificial lipid membrane may be measured. A plurality of electrodes may be provided at the first chamber 107 and the inlet 113 to measure a membrane resistance, a membrane capacity, or a membrane current flowing through the artificial lipid membrane. The other electrical characteristic may be measured.

In accordance with the above configuration and the above operation procedure, (1) since an appropriate amount of lipid solution can be poured to the through hole, it becomes unnecessary to discharge the surplus lipid solution using an external pump, and (2) since the passage through which the lipid solution is poured and the passage through which the electrolytic solution is poured are separately formed, it becomes unnecessary to replace the lipid solution with the electrolytic solution. Therefore, the artificial lipid membrane can be easily formed in a short period of time.

In the present embodiment, the artificial lipid membrane apparatus 100 may be placed in a direction shown in FIG. 1 to be operated or may be placed in the other direction to be operated. The artificial lipid membrane forming apparatus 100 shown in FIG. 1 may be placed in a direction rotated at 90 degrees in a counterclockwise direction in the sheet of FIG. 1 to be operated.

In the present embodiment, it is preferable that a series of steps from the first electrolytic solution pouring step up to the artificial lipid membrane forming step be carried out at 20° C. to 60° C., and it is more preferable that a series of steps from the first electrolytic solution pouring step to the artificial lipid membrane forming step be carried out at 25° C. to 40° C.

In the present embodiment, it is preferable that an analyzing device adopt the above-described artificial lipid membrane forming method. The analyzing device may be used as a clinical examination analyzing device, an electrochemical analyzing device, a gas analyzing device, a taste sense analyzing device, a neurophysiological analyzer, an ion channel analyzer, an ion channel function analyzer, a drug screening analyzing device, or a biosensing device.

Embodiment 2

Hereinafter, the artificial lipid membrane forming method in Embodiment 2 of the present invention will be explained in reference to the drawings.

Figure 8:
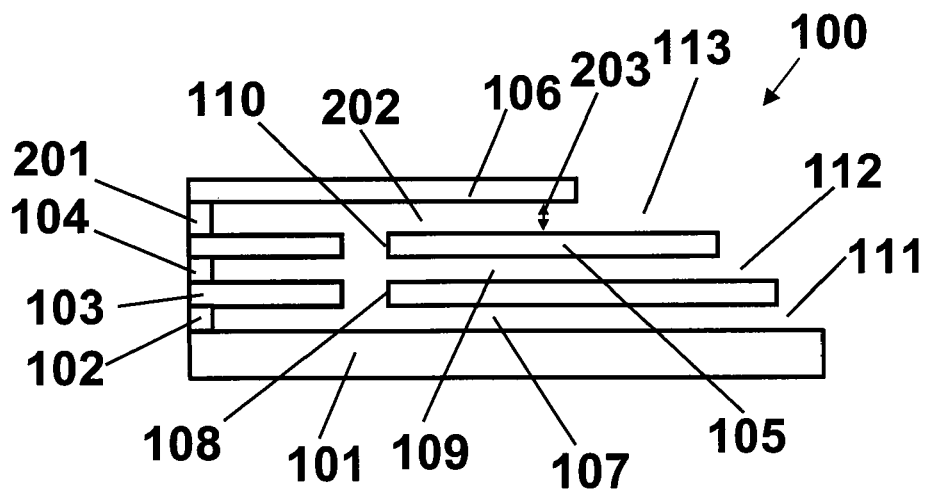
FIGS. 8 (*a*)-(*b*) show a cross-sectional view and an oblique projection view of the artificial lipid membrane forming apparatus in Embodiment 2 of the present invention.
Figure 8:
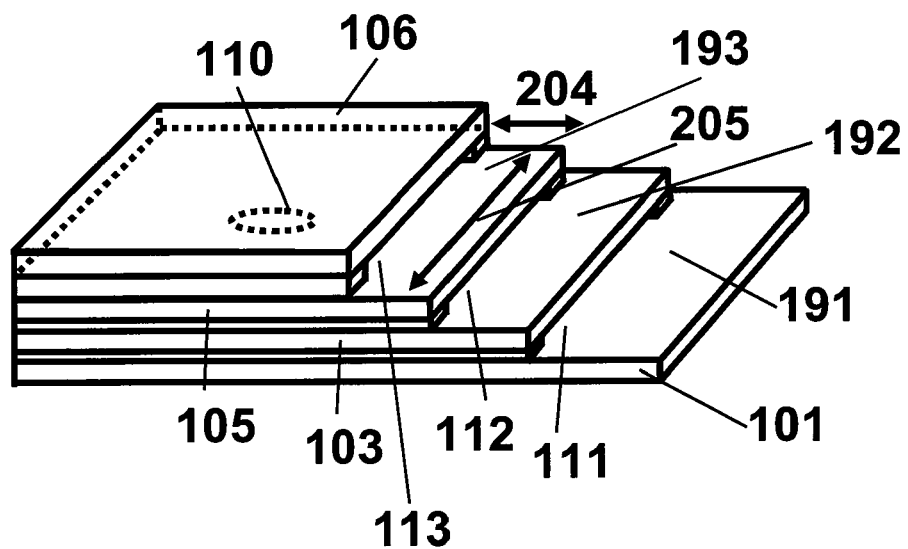

FIGS. 8(a) and 8(b) show a cross-sectional view and an oblique projection view of the artificial lipid membrane forming apparatus in Embodiment 2, respectively. In the present embodiment, the same reference signs are used for the same components as in Embodiment 1, and detailed explanations thereof are omitted.

A difference between the present embodiment and Embodiment 1 is the shape of the inlet 113. Another difference between the present embodiment and Embodiment 1 is the second electrolytic solution pouring step.

As shown in FIG. 8(a), the artificial lipid membrane forming apparatus 100 comprises a third spacer 201. The cover 106 is provided at one end of the third spacer 201. A third chamber 202 is formed between the second thin film 105 and the cover 106. It is preferable that a height 203 of the third chamber 202 be from 10 nm to 100 mm, and it is more preferable that the height 203 be from 10 nm to 1 mm. The height 203 of the third chamber 202 may be constant or may not be constant in the third chamber 202.

Figure 9:
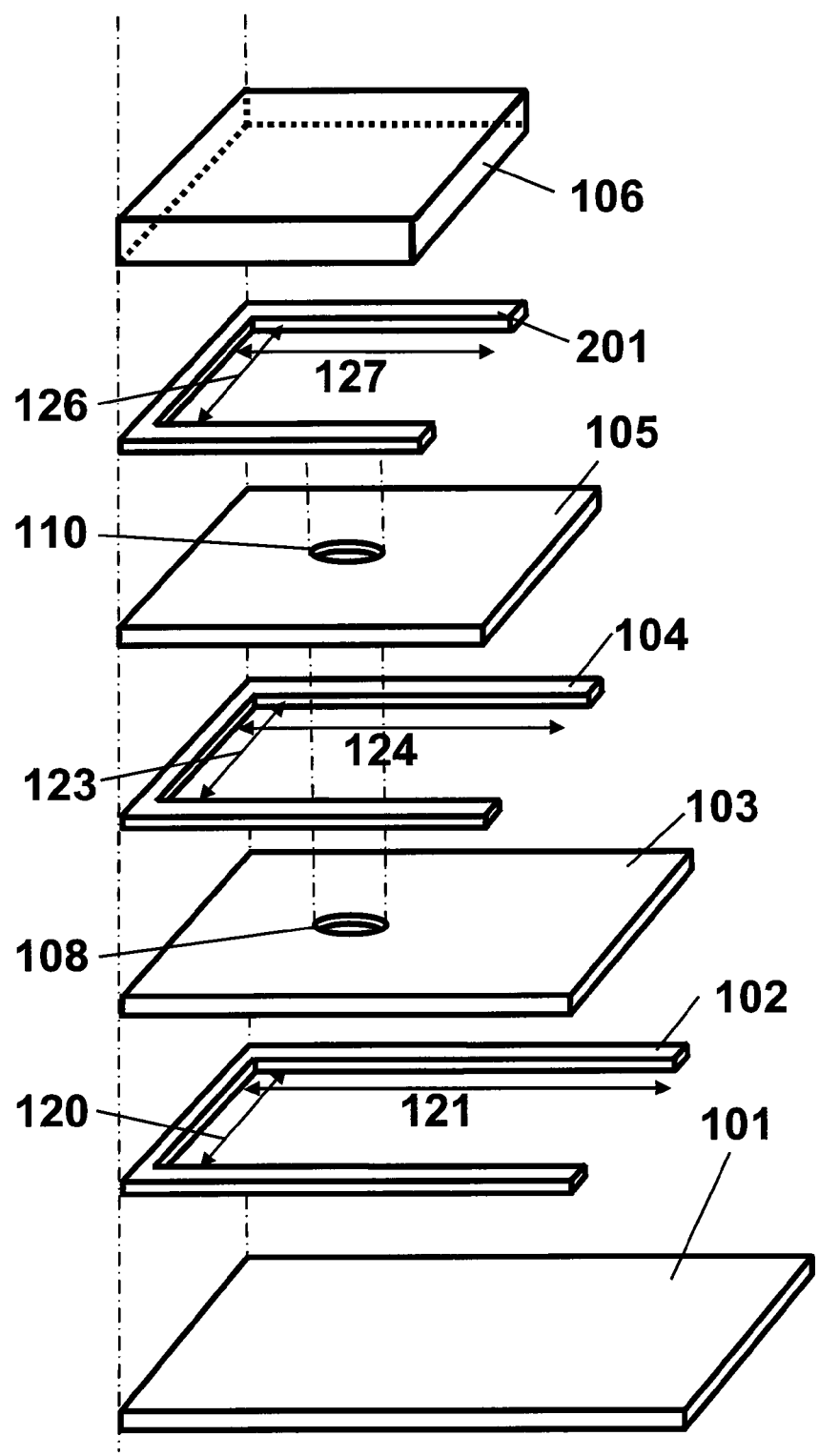
FIG. 9 shows an exploded oblique projection view of the artificial lipid membrane forming apparatus in Embodiment 2 of the present invention.

FIG. 9 shows an exploded oblique projection view of the artificial lipid membrane forming apparatus in Embodiment 2 of the present invention. Each of a width 126 and a length 127 of the third chamber 202 may be constant or may not be constant in the third chamber 202. In the present invention, the shape of the third chamber 202 is not limited. It is most preferable that the shape of the third chamber 202 be a rectangular solid. However, the shape of the third chamber 202 may be the other shape, such as a column or a triangular prism.

It is preferable that the width 126 of the third chamber 202 be from 10 nm to 100 mm, and it is more preferable that the width 126 be from 1 µm to 5 mm. It is preferable that the length 127 of the third chamber 202 be from 10 nm to 100 mm, and it is more preferable that the length 127 be from 1 µm to 5 mm.

As shown in FIG. 8(a), the inlet 113 is formed at one end of each of the second thin film 105 and the cover 106. It is preferable that by causing the position of the end portion of the second thin film 105 and the position of the end portion of the cover 106 to be different from each other, a third overhanging portion 193 be formed, and the inlet 113 be formed. It is preferable that a length 204 of the third overhanging portion 193 of the inlet 113 shown in FIG. 8(b) be from 1 to 10 mm. It is preferable that a width 205 of the third overhanging portion 193 of the inlet 113 be from 1 to 20 mm. The inlet 113 may be flat as shown in FIG. 8(b) or may include a groove structure or a concave-convex structure so as to facilitate the pouring of a liquid.

It is preferable that in the second electrolytic solution pouring step, an appropriate amount of the second electrolytic solution 303 be poured through the inlet 113 to the third chamber 202 by the capillarity. It is preferable that when the second electrolytic solution 303 is poured to the third chamber 202 by the capillarity, at least a part of the outer peripheral surface of the cover 106 be subjected to the hydrophilic treatment. It is preferable that a portion of the outer peripheral surface of the cover 106 which portion contacts the second electrolytic solution 303 be subjected to the hydrophilic treatment. It is preferable that a portion of the outer peripheral surface of the cover 106 which portion is located in the vicinity of the second through hole 110 be subjected to the hydrophilic treatment. In order to impart hydrophilicity to at least a part of the outer peripheral surface of the cover 106, the part of the outer peripheral surface of the cover 106 may be subjected to the oxygen plasma treatment or may be covered with the hydrophilic material. The part of the outer peripheral surface of the cover 106 may be subjected to the other generally known hydrophilic treatment.

In the present embodiment, the artificial lipid membrane apparatus 100 may be placed in a direction shown in FIG. 8(a) to be operated or may be placed in the other direction to be operated. The artificial lipid membrane forming apparatus 100 shown in FIG. 8(a) may be placed in a direction rotated at 90 degrees in a counterclockwise direction in the sheet of FIG. 8(a) to be operated.

In accordance with the configuration of the present embodiment, (1) the openings face in the same direction, and (2) the capillarity can be utilized when pouring the second electrolytic solution 303 to the third chamber 202. Therefore, the solution can be easily poured. As a result, the artificial lipid membrane can be easily formed.

Embodiment 3

Hereinafter, the artificial lipid membrane forming method in Embodiment 3 of the present invention will be explained in reference to the drawings.

Figure 10:
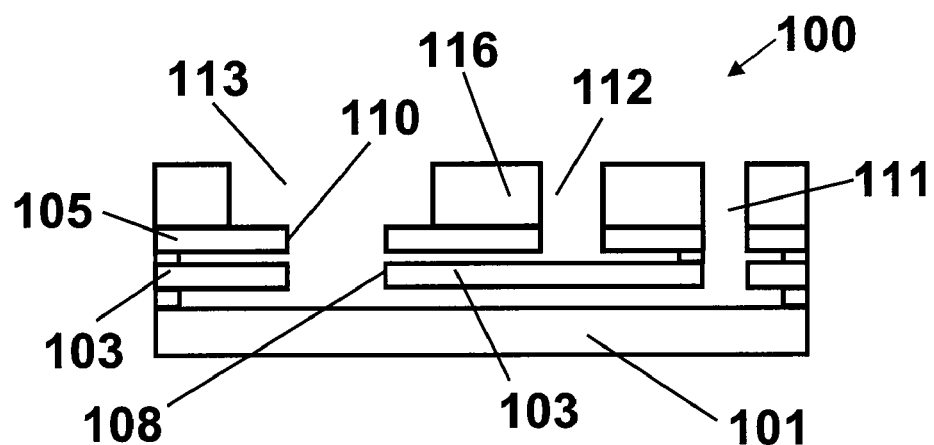
FIGS. 10 (*a*)-(*b*) show a cross-sectional view and an oblique projection view of the artificial lipid membrane forming apparatus in Embodiment 3 of the present invention.
Figure 10:
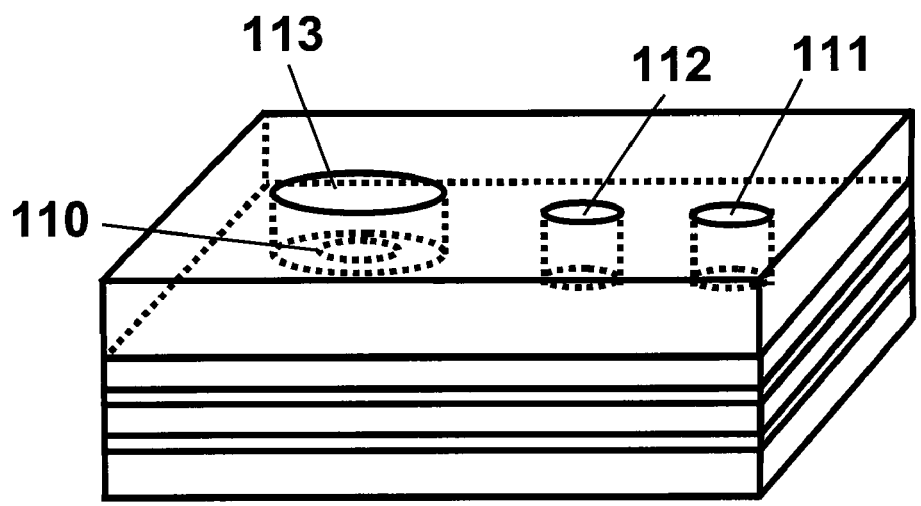

FIGS. 10(a) and 10(b) show a cross-sectional view and an oblique projection view of the artificial lipid membrane forming apparatus in Embodiment 3, respectively. In the present embodiment, the same reference signs are used for the same components as in Embodiment 1, and detailed explanations thereof are omitted.

A difference between the present embodiment and Embodiment 1 is the shape of each of the first opening 111 and the second opening 112.

In the present embodiment, as shown in FIG. 10(a), the first opening 111 may be a through hole formed on the first thin film 103, the second thin film 105, and the cover 106.

In the present embodiment, as shown in FIG. 10(b), the second opening 112 may be a through hole formed on the second thin film 105 and the cover 106.

In accordance with the configuration of the present embodiment, (1) the openings face in the same direction, and (2) the solution is unlikely to evaporate since the opening and the inlet can be reduced in size. As a result, the artificial lipid membrane can be easily formed.

Embodiment 4

Hereinafter, the artificial lipid membrane forming method in Embodiment 4 of the present invention will be explained in reference to the drawings.

Figure 11:
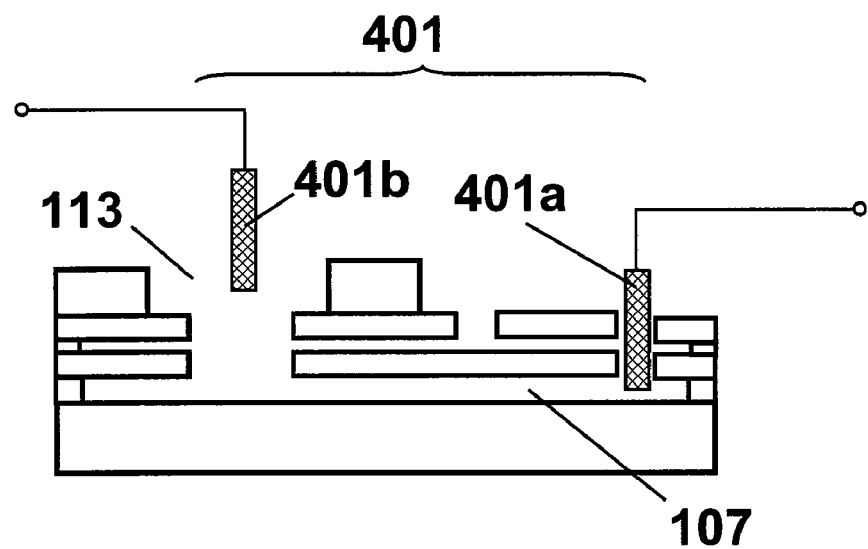
FIG. 11 shows a cross-sectional view and an oblique projection view of the artificial lipid membrane forming apparatus in Embodiment 4 of the present invention.

FIG. 11 shows a cross-sectional view and an oblique projection view of the artificial lipid membrane forming apparatus in Embodiment 4. In the present embodiment, the same reference signs are used for the same components as in Embodiment 1, and detailed explanations thereof are omitted.

A difference between the present embodiment and Embodiment 1 is that an electrode 401 is provided at the first chamber 107 and the inlet 113.

In the present embodiment, one electrode 401 or a plurality of electrodes 401 may be provided. It is preferable that the electrode 401 be an electrode suitable for an electrochemical measurement. It is preferable that the electrode 401 be a non-polarizing electrode. It is most preferable that the electrode 401 be a Ag/AgCl electrode. However, the electrode 401 may be a saturated calomel electrode, or a hydrogen electrode. The electrode 401 may be a metal electrode, such as a Ag electrode, a Pt electrode, or a Au electrode, a carbon electrode, a graphite electrode, or a carbon nanotube electrode. The conductance and/or the electric capacity of the artificial lipid membrane may be measured using the electrodes 401.

Chemical substances, such as ions, enzymes, reaction products, and substrates, contained in the first electrolytic solution 301 or the second electrolytic solution 303 may be measured using the electrode 401. In the present invention, the shape and size of the electrode are not limited.

It is more preferable that the electrode 401 is provided at each of the first chamber 107 and the inlet 113 and in the vicinity of each of the first through hole 108 and the second through hole 110. When electrodes 401a and 401b are respectively provided at the first chamber 107 and the inlet 113 as shown in FIG. 11, the electrodes 401a and 401b may be the same as or different from each other. A plurality of electrodes may be combined.

The electrode 401 may be provided before or after the formation of the artificial lipid membrane. The electrode 401 may be fixed to or detachable from the artificial lipid membrane forming apparatus 100. It is preferable that the electrode 401a provided at the first chamber 107 be formed on the outer peripheral surface of the substrate 101. It is preferable that the electrode 401b provided at the inlet 113 be formed on the outer peripheral surface of the second thin film 105 or the outer peripheral surface of the cover 106.

It is preferable that an amplifier be connected to the electrode 401. It is most preferable that the amplifier be a patch clamp amplifier. However, the amplifier, such as a field effect transistor, a bipolar transistor, an operational amplifier, or an actuating amplifier, may be connected to the electrode 401.

In accordance with the configuration of the present embodiment, the progress situation, and end point of respective steps up to the formation of the artificial lipid membrane can be detected using the electrode 401. For example, when two electrodes are provided in the first chamber 107 and measure an electric conductivity therebetween in the first electrolytic solution pouring step, the completion of the pouring of the first electrolytic solution 301 can be easily detected.

Further, since the passage through which the lipid solution is poured and the passage through which the electrolytic solution is poured are separately formed, the electrode immersed in the electrolytic solution is not contaminated by the lipid solution. Therefore, troublesome steps of protecting the surface of the electrode and cleaning the surface of the electrode are not required. On this account, the artificial lipid membrane can be easily formed.

Embodiment 5

Hereinafter, the artificial lipid membrane forming method in Embodiment 5 of the present invention will be explained in reference to the drawings.

Figure 12:
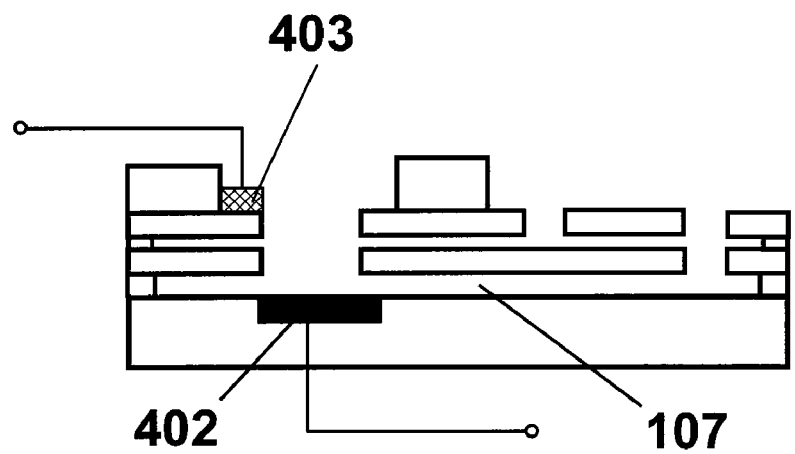
FIG. 12 shows a cross-sectional view and an oblique projection view of the artificial lipid membrane forming apparatus in Embodiment 5 of the present invention.

FIG. 12 shows a cross-sectional view and an oblique projection view of the artificial lipid membrane forming apparatus in Embodiment 5. In the present embodiment, the same reference signs are used for the same components as in Embodiment 1, and detailed explanations thereof are omitted.

A difference between the present embodiment and Embodiment 1 is that a sensor 402 is provided at the first chamber 107.

The sensor 402 may be provided before or after the formation of the artificial lipid membrane. The sensor 402 may be fixed to or detachable from the artificial lipid membrane forming apparatus 100. It is most preferable that the sensor 402 provided at the first chamber 107 be formed on the outer peripheral surface of the substrate 101.

In the present embodiment, it is most preferable that the sensor 402 be a sensor suitable for the electrochemical measurement. It is most preferable that the sensor 402 be an ion electrode or an ion-sensitive field effect transistor (ISFET). It is preferable that the ion electrode be a potassium ion electrode, a sodium ion electrode, a calcium ion electrode, or a chloride ion electrode. It is preferable that the ion-sensitive field effect transistor detect potassium ion, sodium ion, calcium ion, or chloride ion.

The sensor 402 may be an optode, a QCM (Quartz crystal microbalance), a SAW (Surfaceacoustic wave) sensor, a SPR (Surface plasmon resonance), a LSPR (Localizedsurface plasmon microbalance), an organic electrochemical transistor, or an enzyme sensor. A light source or a detector configured to measure an optical property, such as absorbance or reflectivity, may be provided.

In the present invention, the number of sensors 402, and the shape and size of the sensor 402 are not limited. It is more preferable that the sensor 402 is provided at the first chamber 107 and in the vicinity of the first through hole 108. The sensor 402 may be provided at the inlet 113. It is preferable that when the sensor 402 is provided at the inlet 113, it be formed on the outer peripheral surface of the second thin film 105 or the outer peripheral surface of the cover 106.

In the present embodiment, an electrode 403 may be provided at the inlet 113. The electrode 403 may be formed before or after the formation of the artificial lipid membrane. The electrode 403 may be fixed to or detachable from the artificial lipid membrane forming apparatus 100. It is preferable that the electrode 403 be formed on the outer peripheral surface of the second thin film 105 or the outer peripheral surface of the cover 106. The electrode 403 may be provided at the first chamber 107. It is most preferable that when the electrode 403 is provided at the first chamber 107, it be formed on the outer peripheral surface of the substrate 101. The electrode 403 may be formed on the outer peripheral surface of the first thin film 103.

It is preferable that the electrode 403 be an electrode suitable for the electrochemical measurement. It is preferable that the electrode 403 be a non-polarizing electrode. It is most preferable that the electrode 403 be a Ag/AgCl electrode. However, the electrode 403 may be a saturated calomel electrode, or a hydrogen electrode. The electrode 403 may be a metal electrode, such as a Ag electrode, a Pt electrode, or a Au electrode, or may be a carbon electrode, a graphite electrode, or a carbon nanotube electrode. The conductance and/or the electric capacity of the artificial lipid membrane may be measured using the electrodes 403. Chemical substances, such as ions, enzymes, reaction products, and substrates, contained in the first electrolytic solution 301 or the second electrolytic solution 303 may be measured using the electrode 403.

In the present invention, the shape and size of the electrode are not limited. It is more preferable that the electrode 403 is provided at the inlet 113 and in the vicinity of the second through hole 110. The electrode 403 may be used as a reference electrode.

In accordance with the configuration of the present embodiment, the progress situation, and end point of respective steps up to the formation of the artificial lipid membrane can be detected using the sensor 402. For example, when an ion electrode is provided as the sensor 402 at the first chamber 107 in the first electrolytic solution pouring step, the completion of the pouring of the first electrolytic solution 301 can be easily detected.

Further, since the sensor is provided very close to the artificial lipid membrane, noises can be reduced when measuring the electrical characteristic of the artificial lipid membrane. As a result, the formation of the artificial lipid membrane can be easily detected, which is more preferable.

EXAMPLE

First, a method for manufacturing the artificial lipid membrane forming apparatus will be explained. Borosilicate glass was used as the substrate 101. The size of the borosilicate glass was 22 mm×22 mm×0.17 mm. First, the borosilicate glass was subjected to ultrasonic cleaning using pure water for 10 minutes, ethanol for 10 minutes, and acetone for 10 minutes. Next, an outer peripheral surface of the borosilicate glass was subjected to the hydrophilic treatment using UV ozone usher. A treatment time was five minutes.

Each of the first spacer 102, the first thin film 103, the second spacer 104, and the second thin film 105 was a Teflon (trademark) film having a thickness of 100 µm. One Teflon (trademark) film was used for the first spacer 102, the first thin film 103, the second spacer 104, and the second thin film 105. The size of the Teflon (trademark) film was 20 mm×10 mm. One Teflon (trademark) film was bent at its center to be shaped.

Polydimethylsiloxane (PDMS) was used as the cover 106. The polydimethylsiloxane was shaped to form a film having a thickness of 0.5 mm, and a through hole having a diameter of 3 mm was formed such that a solution could be poured therethrough to the second through hole 110.

The first through hole 108 was formed by a drill so as to penetrate both surfaces of the first thin film 103. A diameter of the first through hole 108 was 200 µm.

The second through hole 110 was formed by a drill so as to penetrate both surfaces of the second thin film 105. A diameter of the second through hole 110 was 200 µm.

In order to prevent a positioning error, the first through hole 108 and the second through hole 110 were formed at the same time in a state where the first thin film 103 and the second thin film 105 were laminated on each other.

The first through hole 108 and the second through hole 110 may be respectively formed on the first thin film 103 and the second thin film 105, and then the first thin film 103 and the second thin film 105 may be laminated on each other while adjusting the positions.

The first through hole 108 was formed at a position away from one side of the first thin film 103 by 2 mm, and the second through hole 110 was formed at a position away from one side of the second thin film 105 by 2 mm. It is preferable that the first through hole 108 be formed at a position away from one side of the first thin film 103 by from 0.5 mm to 3 mm, and the second through hole 110 be formed at a position away from one side of the second thin film 105 by from 0.5 mm to 3 mm.

The second opening 112 was formed on the second thin film 105. The second opening 112 was a circular hole penetrating the second thin film 105 and having a diameter of 1 mm. The second opening 112 was formed by a drill.

The first opening 111 was formed on the first thin film 103 and the second thin film 105. The first opening 111 was a circular hole penetrating the first thin film 103 and the second thin film 105 and having a diameter of 1 mm. The first opening 111 was formed using a drill in a state where the first thin film 103 and the second thin film 105 were laminated on each other.

The substrate 101, the first spacer 102, the first thin film 103, the second spacer 104, the second thin film 105, and the cover 106 were laminated on one another. In order to prevent the solution from leaking from the first chamber 107 and the second chamber 109, a peripheral portion of each of the laminated substrate 101, the first spacer 102, the first thin film 103, the second spacer 104, the second thin film 105, and the cover 106 were sealed with an epoxy adhesive. The cover 106 was caused to spontaneously adhere to the second thin film 105.

Finally, the laminated substrate 101, first spacer 102, first thin film 103, second spacer 104, second thin film 105, and cover 106 were sandwiched between two polycarbonate plate (36 mm×36 mm×1 mm), and four corners of the polycarbonate plate were fixed using bolts. A circular hole having a diameter of 9 mm was formed on the polycarbonate contacting the cover 106 such that the solution could be poured to the first opening 111, the second opening 112, and the inlet 113.

Next, a procedure of forming the artificial lipid membrane will be explained. First, the first electrolytic solution pouring step was carried out. A 1M KCl solution was used as the first electrolytic solution 301. The amount of the first electrolytic solution 301 was 1 µL. The first electrolytic solution 301 was dropped to the first opening 111. The dropped first electrolytic solution 301 was poured to the first chamber 107 by the capillarity. Since an inner wall surface of the first chamber 107 was subjected to the hydrophilic treatment, the first electrolytic solution 301 could be easily poured. A time required to pour the first electrolytic solution 301 was one second or less. In the first electrolytic solution pouring step, first, the first chamber 107 was filled with the first electrolytic solution except for the first through hole 108 and a peripheral region of the first through hole 108. Then, the peripheral region of the first through hole 108 and the first through hole 108 were filled with the first electrolytic solution 301. How the first electrolytic solution 301 was poured to the first chamber 107 was observed by an optical microscope.

After the first electrolytic solution pouring step, the lipid solution pouring step was carried out. As the lipid solution 302, a liquid mixture of phosphatide (1,2-diphytanoyl-sn-glycero-3-phosphocholine, Avanti Polar Lipids) and an organic solvent (chloroform, produced by Wako Pure Chemical Industries, Ltd.) was used. The concentration of the lipid solution 302 was 25 mg/mL. The lipid solution 302 was dropped to the second opening 112. The amount of the lipid solution 302 was 0.4 µL. The lipid solution 302 was poured through the second chamber 109 to the first through hole 108 and the second through hole 110. The lipid solution 302 was poured by the capillarity. Since an inner wall surface of the second chamber 109 was made from Teflon (trademark) and hydrophobic, the lipid solution 302 could be easily poured. A time required to pour the lipid solution 302 was one second or less. How the lipid solution 302 was poured to the first through hole 108 and the second through hole 110 was observed by the optical microscope.

Next, after the lipid solution pouring step, the second electrolytic solution pouring step was carried out. A 1M KCl solution was used as the second electrolytic solution 303. The amount of the second electrolytic solution 303 was 2 µL. The second electrolytic solution 303 was dropped to the inlet 113. The second electrolytic solution 303 was poured to flow along the inner wall of the inlet 113. A time required to pour the second electrolytic solution 303 was one second or less. How the second electrolytic solution 303 was poured to the inlet 113 was observed visually and by the optical microscope.

Figure 13:
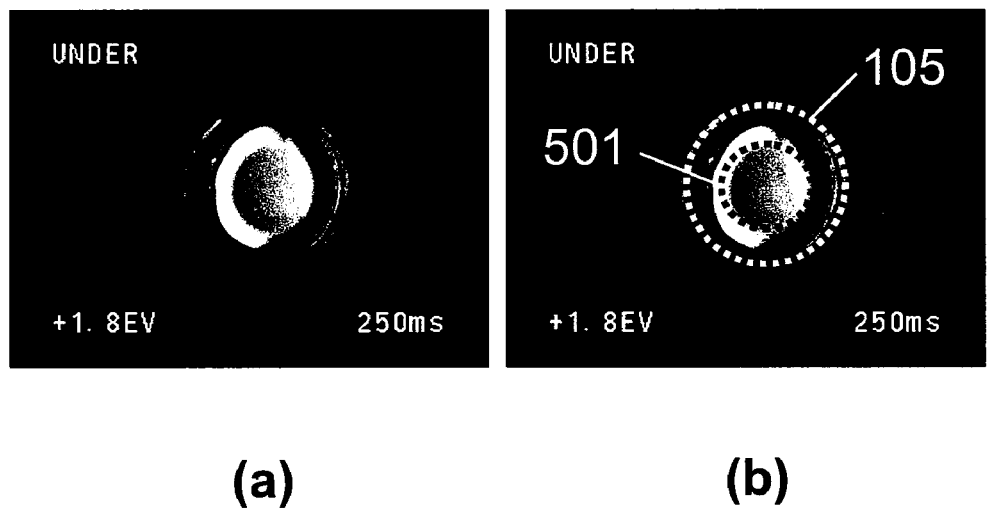
FIGS. 13 (*a*)-(*b*) show micrographs of an artificial lipid membrane in Example of the present invention.

Finally, after the second electrolytic solution pouring step, the artificial lipid membrane forming step was carried out. In the artificial lipid membrane forming step, the process stood by for 10 seconds. In order to confirm that the artificial lipid membrane was formed through the artificial lipid membrane forming step, the artificial lipid membrane was observed by an optical microscope. When the artificial lipid membrane is formed, it is observed as a so-called black membrane. This is because the artificial lipid membrane has a thickness of about 2 to 5 nm and is less likely to reflect light. FIGS. 13($a$) and 13($b$) show micrographs of the artificial lipid membrane. FIG. 13($b$) clearly shows by a white dotted line a boundary of the first through hole 108 and a region 501 of the artificial lipid membrane in FIG. 13($a$). In FIG. 13($b$), the region 501 appeared to be darker than its periphery. It was observed that the area of the region 501 increased with time, and the artificial lipid membrane gradually became a thin film.

Figure 14:
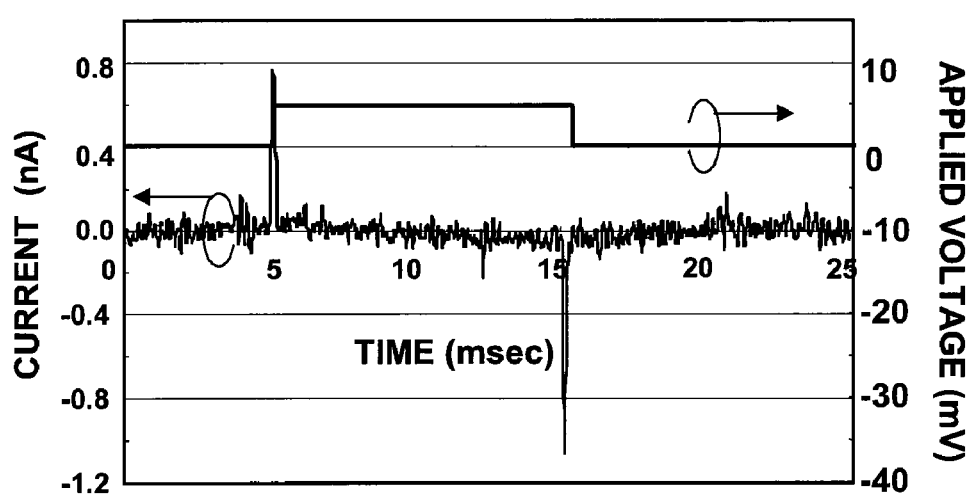
FIG. 14 shows a graph showing a transient response of a current flowing through the artificial lipid membrane in Example of the present invention.

Further, in order to measure the electrical characteristic of the artificial lipid membrane, the electrode 401$a$ and the electrode 401$b$ were respectively provided at the first opening 111 and the inlet 113. A patch clamp amplifier (EPC-10, HEKA) was used to measure the electrical characteristic. The electrode 401$a$ was connected to a ground wire, and the electrode 401$b$ was connected to a signal wire. A pulse voltage of 5 mV was applied to the electrode 401$a$ toward the electrode 401$b$ for 10 msec. A transient response of a current flowing through the artificial lipid membrane was recorded. FIG. 14 shows the transient response of the current flowing through the artificial lipid membrane. As the transient response, the membrane current due to the electric capacity of the artificial lipid membrane was measured.

In contrast, when the artificial lipid membrane was not formed, and the first electrolytic solution 301 in the first chamber 107 and the second electrolytic solution 303 in the inlet 113 directly contacted each other, the electric-capacity membrane current shown in FIG. 14 was not measured.

Further, in accordance with the above-described procedure of forming the artificial lipid membrane, the artificial lipid membrane was formed while the electrode 401$a$ and the electrode 401$b$ respectively formed at the first opening 111 and the inlet 113 did not contact the lipid solution 302 and the clean electrode surfaces were maintained. As a result, the electrical characteristic of the artificial lipid membrane were normally measured.

Comparative Example

The artificial lipid membrane was formed using the foam spraying method that is one of the conventional artificial lipid membrane forming methods.

Figure 15:
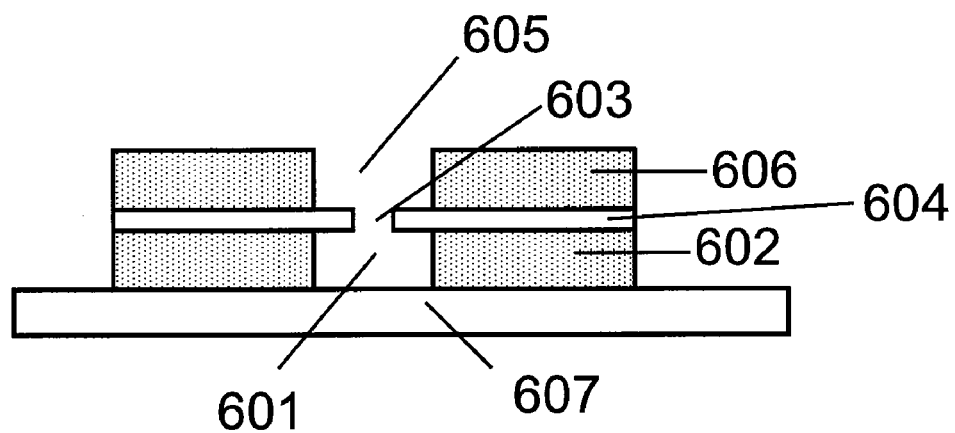
FIG. 15 shows a diagram showing the artificial lipid membrane forming apparatus in Comparative Example.

FIG. 15 shows the artificial lipid membrane forming apparatus of Comparative Example. A first chamber 601 was formed by opening a circular through hole having a diameter of 1.5 mm on a thin film 602. The first chamber 601 was formed by punching. Polydimethylsiloxane was used as the thin film 602. The size of the thin film 602 was 10 mm×10 mm×0.5 mm. A through hole 603 at which the artificial lipid membrane is formed was formed by opening a circular through hole having a diameter of 200 μm on a Teflon (trademark) film 604 having a thickness of 100 μm. The through hole 603 was formed by a drill. An inlet 605 was formed by opening a circular through hole having a diameter of 1.5 mm on a thin film 606. The inlet 605 was formed by the punching. Polydimethylsiloxane was used as the thin film 606. The size of the thin film 606 was 10 mm×10 mm×0.5 mm. Then, as shown in FIG. 15, the Teflon (trademark) film 604, the thin film 602, and the thin film 606 were laminated on a glass substrate 607. Borosilicate glass was used as the glass substrate 607. The size of the glass substrate 607 was 22 mm×22 mm×0.17 mm.

Next, the steps of the artificial lipid membrane forming method will be explained. First, the electrolytic solution was poured to the first chamber 601 using a micro pipette. A 1M KCl was used as the electrolytic solution. The amount of the electrolytic solution poured was 1 μL. Next, the Teflon (trademark) film 604 was laminated on the thin film 602. The surplus electrolytic solution was removed. Next, the thin film 606 was laminated on the Teflon (trademark) film 604. Then, the electrolytic solution was poured to the inlet 605 using the micro pipette. A 1M KCl was used as the electrolytic solution. The amount of the electrolytic solution poured was 1 μL. Finally, the lipid solution was sprayed to the through hole 603 using the micro pipette. As the lipid solution, a liquid mixture of phosphatide (1,2-diphytanoyl-sn-glycero-3-phosphocholine, Avanti Polar Lipids) and an organic solvent (chloroform, produced by Wako Pure Chemical Industries, Ltd.) was used. The concentration of the lipid solution was 25 mg/mL.

Figure 16:
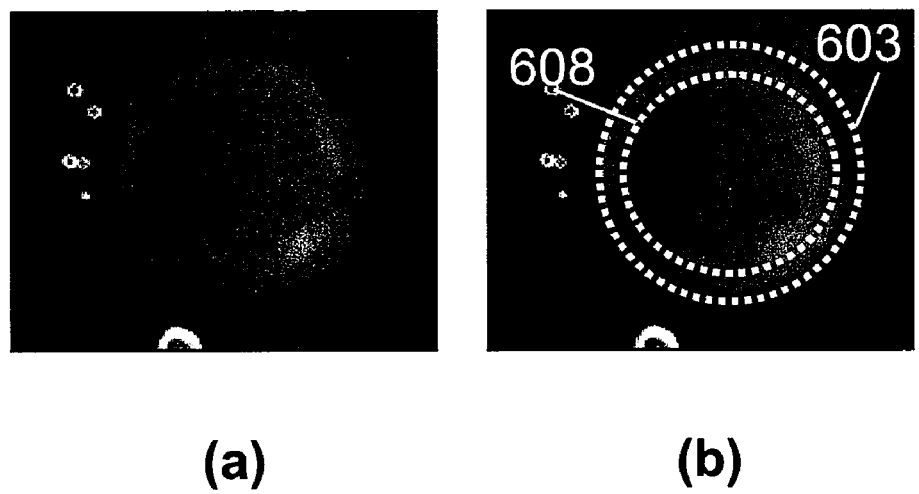
FIGS. 16 (*a*)-(*b*) show micrographs of the artificial lipid membrane in Comparative Example.

The artificial lipid membrane formed was observed by an optical microscope. FIGS. 16($a$) and 16($b$) show optical micrographs of the artificial lipid membrane of Comparative Example. FIG. 16($b$) clearly shows by a white dotted line a boundary of the through hole 603 and a region 608 of the artificial lipid membrane in FIG. 16($a$). In FIG. 16($b$), the region 608 appeared to be darker than its periphery. It was observed that the area of the region 608 increased with time, and the artificial lipid membrane gradually became a thin film.

Figure 17:
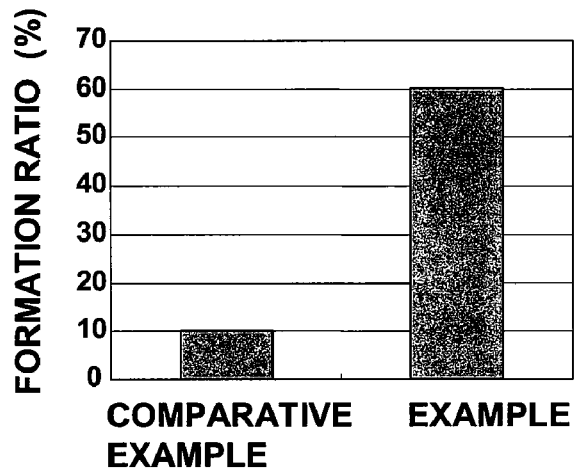
FIG. 17 shows a comparison diagram of a formation ratio of the artificial lipid membrane.
Figure 18:
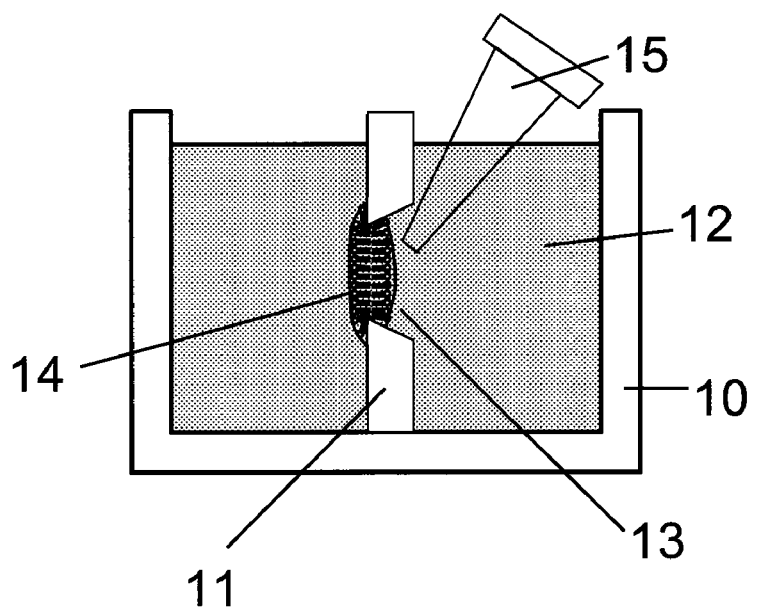
FIG. 18 shows a schematic diagram of a conventional artificial lipid membrane forming apparatus (foam spraying method).
Figure 19:
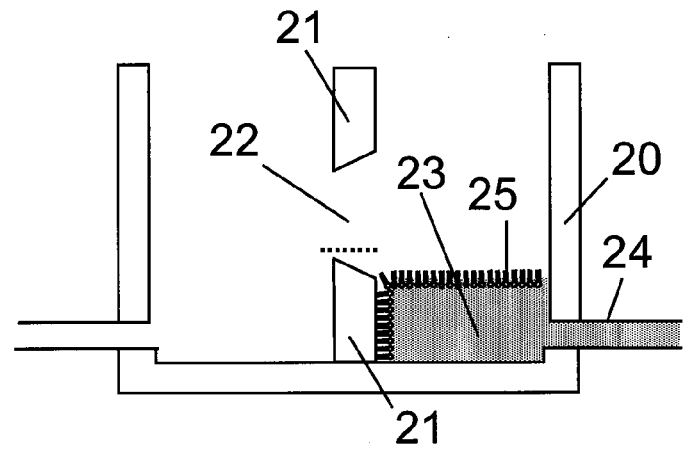
FIGS. 19 (*a*)-(*c*) show schematic diagrams of the conventional artificial lipid membrane forming apparatus (attaching method).
Figure 19:
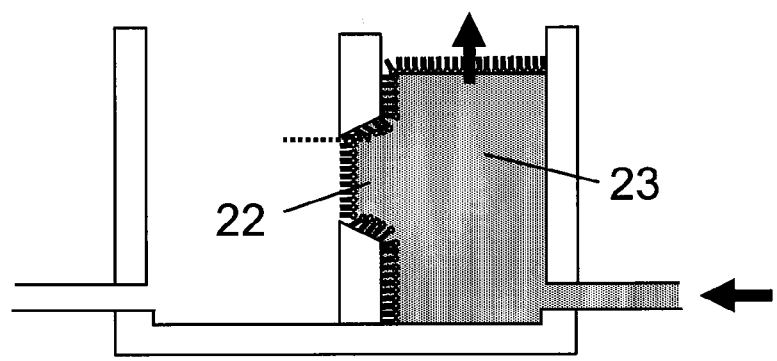
Figure 19:
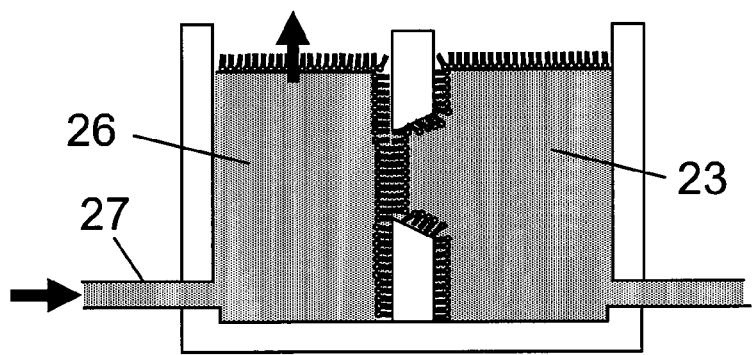
Figure 20:
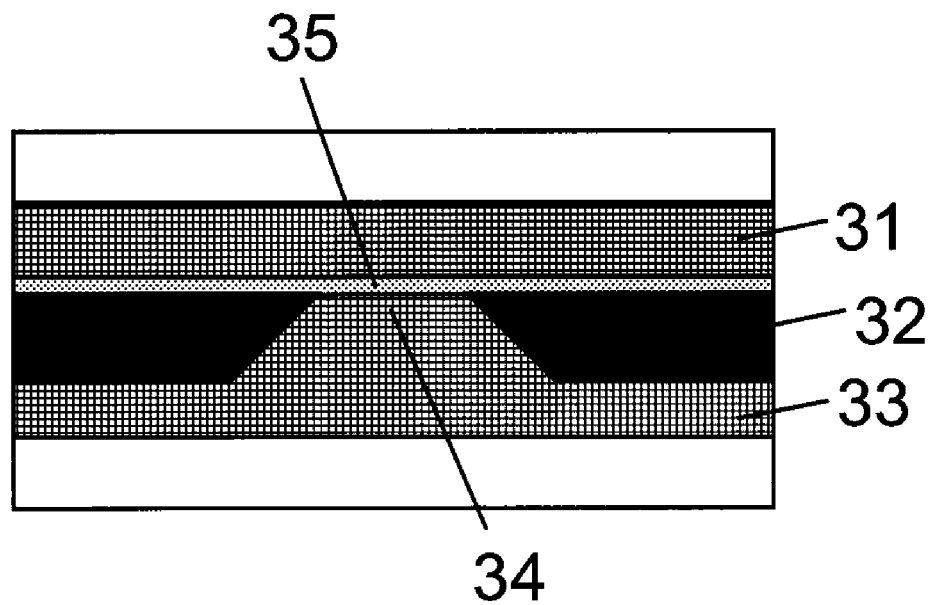
FIG. 20 shows a schematic diagram of the conventional artificial lipid membrane forming apparatus (PTL 1).

FIG. 17 is a comparison diagram of a formation ratio of the artificial lipid membrane in Example of the present invention and Comparative Example. Herein, the formation ratio denotes a numerical value obtained by dividing the number of times of the formation of the artificial lipid membrane by the number of trials and then multiplying the obtained number by 100. Specifically, the formation of the artificial lipid membrane was tried ten times in each of Example and Comparative Example. As a result, the artificial lipid membrane was formed at the formation ratio of 60% in Example and 10% in Comparative Example. This result shows that Example of the present invention can form the artificial lipid membrane at a high ratio by a simple operation as compared to the conventional example.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the spirit of the present invention.

INDUSTRIAL APPLICABILITY

In accordance with the present invention, since an appropriate amount of lipid solution can be introduced to a through hole, it is unnecessary to provide an external pump configured to discharge a surplus lipid solution, and it is unnecessary to stand by for a long period of time. As a result, the artificial lipid membrane can be easily formed in a short period of time as compared to the conventional artificial lipid membrane forming method and artificial lipid forming apparatus.

If the artificial lipid membrane can be easily formed in a short period of time, various analyzing operations utilizing the artificial lipid membrane can be significantly improved in efficiency. For example, the artificial lipid membrane incorporating a membrane protein, such as an ion channel or a receptor, can be used for a basic structure analysis of a membrane protein, a function elucidation of the membrane protein, and a correlation research between the membrane proteins. The present invention can directly contribute to the above-described research development, and in addition, the present invention is applicable to a medical and pharmaceutical field, such as diagnosis of disease caused by the ion channel and screening of a new drug development. Moreover, the present invention is applicable to a biosensor and the like by utilizing a specific molecular recognition of the membrane protein.

REFERENCE SIGNS LIST 10 container
11 flat plate
12 electrolytic solution
13 minute hole
14 lipid solution
15 pipette
20 container
21 flat plate
22 minute hole
23 electrolytic solution
24 inlet
25 lipid molecule
26 electrolytic solution
27 inlet
31 first chamber
32 dividing wall
33 second chamber
34 small hole
35 artificial lipid membrane
100 artificial lipid membrane forming apparatus
101 substrate
102 first spacer
103 first thin film
104 second spacer
105 second thin film
106 cover
107 first chamber
108 first through hole
108a, 108b cross section
109 second chamber
110 second through hole
110a, 110b cross section
110c inner wall surface
111 first opening
112 second opening
113 inlet
113a inner wall surface
114 height of first chamber
115 height of second chamber
120 width of first chamber
121 length of first chamber
122 diameter of first through hole
123 width of second chamber
124 length of second chamber
125 diameter of second through hole
126 width of third chamber
127 length of third chamber
130 length of overhanging portion of first opening
131 width of overhanging portion of first opening
132 length of overhanging portion of second opening
133 width of overhanging portion of second opening
134 diameter of inlet
191 first overhanging portion
192 second overhanging portion
193 third overhanging portion
201 third spacer
202 third chamber
203 height of third chamber
204 length of overhanging portion of inlet
205 width of overhanging portion of inlet
301 first electrolytic solution
302 lipid solution
303 second electrolytic solution
401, 401a, 401b electrode
402 sensor
403 electrode
501 region
601 first chamber
602 thin film
603 through hole
604 Teflon (trademark) film
605 inlet
606 thin film
607 glass substrate
608 region

The invention claimed is:

1. A method for forming an artificial lipid membrane using an artificial lipid membrane forming apparatus comprising in the following order,
an apparatus preparing step of preparing the apparatus comprising:
a substrate;
a first spacer disposed at one end of the substrate;
a first thin film disposed on the substrate via the first spacer;
a second spacer disposed at one end of the first thin film;
a second thin film disposed on the first thin film via the second spacer; and
a cover disposed at one end of the second thin film, wherein:
a first chamber is formed between the substrate and the first thin film;
the first thin film comprises a first through hole penetrating both surfaces thereof;
a second chamber is formed between the first thin film and the second thin film;
the second thin film comprises a second through hole penetrating both surfaces thereof;
the cover has an inlet connected to the second through hole;
the first through hole overlaps the second through hole in plan view; and
the first chamber is connected to the inlet via the first through hole and the second through hole,
a first electrolytic solution pouring step of pouring an electrolytic solution to the first chamber;
a lipid solution pouring step of pouring a lipid solution through the second chamber to at least one of the first through hole or the second through hole; and
a second electrolytic solution pouring step of pouring the electrolytic solution to the inlet to form the artificial lipid membrane inside the through hole to which the lipid solution is poured.

2. The method according to claim 1, wherein the first thin film, the first spacer, and the second thin film are integrally formed.

3. The method according to claim 1, wherein a cross-sectional area of the first through hole is the same as a cross-sectional area of the second through hole.

4. The method according to claim 1, wherein the inlet overlaps the first chamber in plan view.

5. The method according to claim 1, wherein an outer peripheral surface of the first chamber is hydrophilic.

6. The method according to claim 1, wherein an outer peripheral surface of the second chamber is hydrophobic.

7. The method according to claim 1, wherein an outer peripheral surface of the inlet is hydrophilic.

8. The method according to claim 1, wherein at least one of the first chamber and the inlet comprises an electrode.

9. The method according to claim 1, wherein at least one of the first chamber and the inlet comprises a sensor.

10. The method according to claim 1, wherein in the first electrolytic solution pouring step, the electrolytic solution is poured to the first chamber by capillarity.

11. The method according to claim 1, wherein in the lipid solution pouring step, the lipid solution is poured to at least one of the first through hole and the second through hole by capillarity.

12. An artificial lipid membrane forming apparatus comprising:
a substrate;
a first spacer disposed at one end of the substrate;
a first thin film disposed on the substrate via the first spacer;
a second spacer disposed at one end of the first thin film;
a second thin film disposed on the first thin film via the second spacer; and
a cover disposed at one end of the second thin film, wherein:
a first chamber is formed between the substrate and the first thin film;
the first thin film comprises a first through hole penetrating both surfaces thereof;
a second chamber is formed between the first thin film and the second thin film;
the second thin film comprises a second through hole penetrating both surfaces thereof;
the cover has an inlet connected to the second through hole;
the first through hole overlaps the second through hole in plan view; and
the first chamber is connected to the inlet via the first through hole and the second through hole.

13. The artificial lipid membrane forming apparatus according to claim 12, wherein the first thin film, the first spacer, and the second thin film are integrally formed.

14. The artificial lipid membrane forming apparatus according to claim 12, wherein a cross-sectional area of the first through hole is the same as a cross-sectional area of the second through hole.

15. The artificial lipid membrane forming apparatus according to claim 12, wherein the inlet overlaps the first chamber in plan view.

16. The artificial lipid membrane forming apparatus according to claim 12, wherein an outer peripheral surface of the first chamber is hydrophilic.

17. The artificial lipid membrane forming apparatus according to claim 12, wherein an outer peripheral surface of the second chamber is hydrophobic.

18. The artificial lipid membrane forming apparatus according to claim 12, wherein an outer peripheral surface of the inlet is hydrophilic.

19. The artificial lipid membrane forming apparatus according to claim 12, wherein at least one of the first chamber and the inlet comprises an electrode.

20. The artificial lipid membrane forming apparatus according to claim 12, wherein at least one of the first chamber and the inlet comprises a sensor.

\* \* \* \* \*